(12) United States Patent
Crooks et al.

(10) Patent No.: US 7,091,357 B2
(45) Date of Patent: Aug. 15, 2006

(54) CHAIN-MODIFIED PYRIDINO-N SUBSTITUTED NICOTINE COMPOUNDS FOR USE IN THE TREATMENT OF CNS PATHOLOGIES

(75) Inventors: Peter A. Crooks, Nicholasville, KY (US); Linda Dwoshin, Lexington, KY (US); Rui Xu, Longmont, CO (US); Joshua T. Ayers, Chadds Ford, PA (US)

(73) Assignee: University of Kentucky Research Foundation, Lexington, KY (US)

( * ) Notice: Subject to any disclaimer, the term of this patent is extended or adjusted under 35 U.S.C. 154(b) by 65 days.

(21) Appl. No.: 10/328,192

(22) Filed: Dec. 26, 2002

(65) Prior Publication Data

US 2003/0225142 A1    Dec. 4, 2003

Related U.S. Application Data

(60) Provisional application No. 60/342,120, filed on Dec. 26, 2001.

(51) Int. Cl.
*C07D 401/04* (2006.01)
(52) U.S. Cl. .................................. 546/279.4
(58) Field of Classification Search .............. 546/279.4
See application file for complete search history.

(56) References Cited

U.S. PATENT DOCUMENTS

| | | | |
|---|---|---|---|
| 5,278,176 A | 1/1994 | Lin | |
| 5,574,052 A | 11/1996 | Rose et al. | |
| 5,691,365 A | 11/1997 | Crooks et al. | |
| 5,736,560 A | 4/1998 | Cosford et al. | |
| 5,776,956 A | 7/1998 | Rolf | |
| 5,824,692 A | 10/1998 | Lippiello et al. | |
| 5,840,906 A | 11/1998 | Zoltewicz et al. | |
| 5,846,983 A | 12/1998 | Sandborn et al. | |
| 5,861,407 A | 1/1999 | Curtis et al. | |
| 5,889,029 A | 3/1999 | Rolf | |
| 5,976,523 A | 11/1999 | Awaya et al. | |
| 6,004,950 A | 12/1999 | Friesen et al. | |
| 6,034,079 A | 3/2000 | Sanberg et al. | |
| 6,110,947 A | 8/2000 | Ito | |
| 6,114,361 A | 9/2000 | Robinson et al. | |
| 6,121,289 A | 9/2000 | Houdi | |
| 6,156,748 A | 12/2000 | Panetta et al. | |
| 6,166,044 A | 12/2000 | Sandborn et al. | |
| 6,194,581 B1 | 2/2001 | Cosford et al. | |
| 6,218,383 B1 | 4/2001 | Bencherif | |
| 6,239,146 B1 | 5/2001 | Vrudhula et al. | |
| 6,262,089 B1 | 7/2001 | Hertel et al. | |
| 6,277,870 B1 | 8/2001 | Gurley et al. | |
| 6,297,262 B1 | 10/2001 | Sams-Dodd et al. | |

OTHER PUBLICATIONS

Noguchi et al., "Conguate of nicotine, etc" CA 89:125658 (1978).*
Moehrle et al., "Isomeric 1-phenul, etc." CA 86:90110 (1977).*
Von Euler et al., "Neurotransmitter releasing, etc.," CA 72:88531 (1970).*
Pilotti et al., "Studies on the indentification, etc.," CA 86:715 (1977).*
Obi et al., "Reaction products of nicotine, etc.," CA 69:16898 (1968).*

* cited by examiner

*Primary Examiner*—Patricia L. Morris
(74) *Attorney, Agent, or Firm*—McDermott Will & Emery LLP

(57) ABSTRACT

Compounds for treating abuse of nicotinic receptor agonists, addiction to psychostimulant drugs, addiction to opiates, addiction to alcohol, addiction to tobacco products, addiction to nicotine, schizophrenia and related diseases, depression and related conditions, Alzheimer's disease, Parkinson's disease, irritable bowel syndrome, and colitis. The compounds competitively inhibit central nervous system acting nicotinic receptor agonists and act at the putative α3β2* and α4β2 neuronal nicotinic receptors in the central nervous system.

15 Claims, No Drawings

CHAIN-MODIFIED PYRIDINO-N SUBSTITUTED NICOTINE COMPOUNDS FOR USE IN THE TREATMENT OF CNS PATHOLOGIES

RELATED APPLICATIONS

This application claims priority from U.S. Provisional Patent Application Ser. No. 60/342,120, filed Dec. 26, 2001.

FIELD OF THE INVENTION

This invention relates to chain-modified analogs of N-n-octylnicotinium iodide (NONI) and N-n-decylnicotinium iodide (NDNI) that have selective $\alpha_3\beta_2*$ and $\alpha_4\beta_2$ nicotinic receptor antagonist properties respectively, and to a method of using such compounds to treat central nervous system pathologies. The present invention also relates to pharmaceutical compositions containing these compounds, as well as various uses thereof.

BACKGROUND OF THE INVENTION

Formula (I) below shows the structure of S-(−)-nicotine (NIC), which activates neuronal nicotinic receptors evoking release of dopamine (DA) from presynaptic terminals in the central nervous system (CNS). NIC is a legal substance of dependence that produces many of its effects on the CNS, some of which may be considered to be beneficial e.g., mood elevation, arousal and learning and memory enhancement. NIC produces its effect by binding to a family of ligand-gated ion channels, stimulation by acetylcholine (ACh) or NIC causes the ion channel to open, and cations to flux with a resulting rapid (in millisec) depolarization of the target cell.

Over the last 12 years, there has been a substantial increase in studies on brain nicotinic receptors. Adult peripheral nicotinic muscle receptors are composed of four subunit domains: $2\alpha$, $\beta$, $\gamma$ and $\delta$. Traditional peripheral nicotinic receptor antagonists are shown in formula (II) and (III), i.e. decylmethonium (DEC) (muscle), hexamethonium (HEX) (ganglionic), and d-tubocurarine (d-Tc) (muscle). These compounds have also shown the ability to weakly inhibit neuronal nicotinic receptors.

Neuronal nicotinic receptors are composed of only two subunits, $\alpha$ and $\beta$ and are believed to assemble with the general stoichiometry of $2\alpha$ and $3\beta$. Nine subtypes of the $\alpha$ subunit ($\alpha 2$ to $\alpha 10$) and three subtypes of the $\beta$ unit ($\beta 2$ to $\beta 4$) are found in CNS. The most common nicotinic receptor species in the brain is composed of two $\alpha 4$ and three $\beta 2$ subunits, i.e., $\alpha 4 \beta 2$. These subunits display different, but overlapping, patterns of expression in the brain.

For the most part, the actual subunit compositions and stoichiometries of nicotinic receptors in the brain remain to be elucidated. Thus, neuronal nicotinic receptor subtype diversity originates from differences in the amino acid sequence at the subunit level and from the multiple combinations of assemblies of subunits, which can form functional receptor proteins.

In spite of the extensive diversity in neuronal nicotinic receptor messenger RNA expression, only a limited number of tools are available to study the pharmacology of native receptors. Radioligands are used in many such studies. [$^3$H]NIC appears to label the same sites in the brain as [$^3$H]ACh. It has been estimated that over 90% of [$^3$H]NIC binding in the brain is due to association with the heteromeric receptor that is composed of $\alpha 4$ and $\beta 2$ subunits. Also abundant in the CNS, are the receptors labeled by [$^3$Hmethyllycaconitine (MLA), which has high affinity for the $\alpha 7$ homomeric nicotinic receptor subtype. Additionally, nicotinic receptor subtypes can be studied using functional assays such as NIC-evoked [$^3$H]dopamine (DA) release from rat striatal slices. Nicotinic receptors are located on the cell body and terminals of the nigrostiatal pathway. NIC facilitates DA release from striatal nerve terminals. Studies strongly suggest that the [$^3$H]DA release assay is useful to probe $\alpha_3\beta_2*$ nicotinic receptor subtypes.

Structural and functional diversity of CNS nicotinic receptors has stimulated a great deal of interest in developing novel, subtype-selective agonists. Some of these agonists are currently being evaluated in clinical trials for cognitive enhancement and neuroprotective effects potentially beneficial for disease states such as Alzheimer's and Parkinson's Disease. Surprisingly, little attention has been focused on developing subtype-selective antagonists for neuronal nicotinic receptors. Potential uses of nicotinic receptor anatagonists are for the treatment of psychostimulant abuse, smoking cessation, and schizophrenia.

A class of pyridino N-substituted nicotine analogs having formula (IV) below are known antagonists that have affinity in the [$^3$H]NIC binding assay and demonstrate the ability to inhibit NIC-evoked [$^3$H]DA release. The abbreviated nomenclature is given in parentheses.

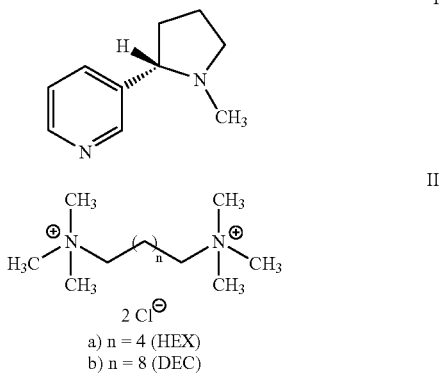

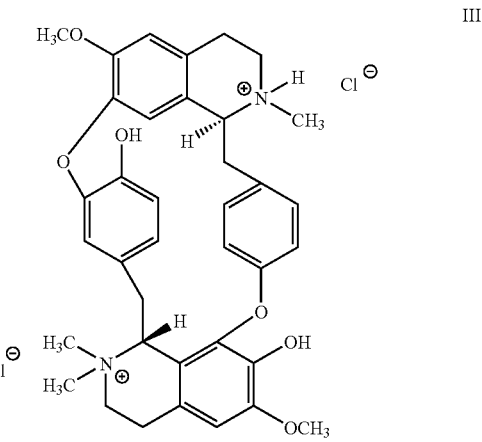

-continued

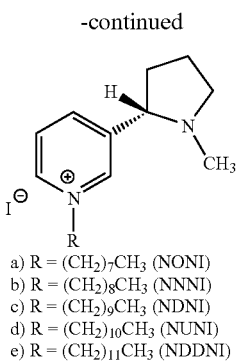

a) R = (CH₂)₇CH₃ (NONI)
b) R = (CH₂)₈CH₃ (NNNI)
c) R = (CH₂)₉CH₃ (NDNI)
d) R = (CH₂)₁₀CH₃ (NUNI)
e) R = (CH₂)₁₁CH₃ (NDDNI)

These compounds are useful in the treatment of nicotine abuse, smoking cessation therapy, as an antidote for nicotine intoxication, treatment of cognitive disorders such as Alzheimer's disease and for the treatment of Parkinson's disease. These compounds and their method of use were the subject of U.S. Pat. No. 5,691,365, issued Nov. 25, 1997. The content of this patent is incorporated herein by reference.

The invention disclosed herein is directed to a series of efficacious and subtype-selective nicotinic antagonists at nicotinic receptors in the CNS. These compounds comprise alkenyl alkynyl, branched and cyclic pyridine-N substituted NIC analogs.

SUMMARY OF THE INVENTION

The present invention provides for chain-modified analogs of N-n-octylnicotinium iodide (NONI) and N-n-decylnicotinium iodide (NDNI) having potent and selective antagonistic activity at certain neuronal nicotinic receptor subtypes. These compounds competitively inhibit CNS nicotinic receptor agonists and act at $\alpha_3\beta_2^*$ or $\alpha_4\beta_2$ neuronal nicotinic receptor subtypes in the CNS.

A preferred embodiment of the invention provides for a method of antagonizing the nicotinic receptor comprising administering of a pharmaceutically effective amount of a compound of the invention.

Still another embodiment the invention provides a method for the treatment of psychostimulant abuse (including nicotine abuse, amphetamine abuse, methamphetamine abuse, and cocaine abuse), alcohol abuse, as a smoking cessation therapy, as an antidote for nicotine intoxication comprising administering of a pharmaceutically effective amount of a compound according to the invention, as a therapeutic agent for the treatment of pathologies of the GI tract, including irritable bowel syndrome, colitis and related disorders.

This invention further provides a method of treatment of CNS disorders associated with the alteration of normal neurotransmitter release in the brain, including conditions such as Alzheimer's disease as well as other types of dementia, Parkinson's disease, cognitive dysfunction (including disorders of attention, focus and concentration), attention deficit syndrome, affective disorders, mood and emotional disorders such as depression, panic anxiety and psychosis, Tourette's syndrome, schizophrenia, eating disorders and the control of pain comprising administering of a pharmaceutically effective amount of a compound according to the invention.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DETAILED DESCRIPTION OF THE INVENTION

The present invention provides novel compounds, including resolved enantiomers and diastereoisomers, having a formula selected from formula (V) or formula (VI) below:

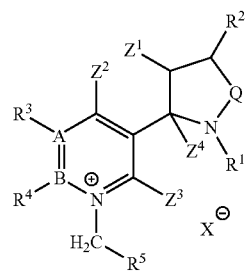

(V)

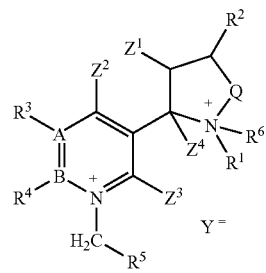

(VI)

wherein

Q is selected from the group consisting of a straight chain or branched alkylene group having 1–3 carbon atoms, a substituted alkenylene group having 1–3 carbon atoms, C(O), O, C(S), S, S(O) and S(O)₂ containing alkylene moiety, provided that any heteroatom contained in Q is separated from N by at least one carbon atom;

$R^1$ is selected from the group consisting of hydrogen, lower straight chain or branched alkyl, cycloalkyl having 1–6 carbon atoms, substituted cycloalkyl having 1–6 carbon atoms, aryl, aralkyl, or heterocyclic group;

$R^2$, $Z^1$ and $Z^4$ are each independently selected from the group consisting of hydrogen, lower alkyl, lower branched alkyl, lower alkenyl, and lower branched alkenyl;

A and B are selected from nitrogen or carbon with the proviso that when A or B is nitrogen, $R^3$ or $R^4$ cannot be present;

$R^3$, $R^4$, $Z^2$ and $Z^3$ are each independently selected from the group consisting of hydrogen; alkyl; substituted alkyl; cycloalkyl; substituted cycloalkyl; substituted alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl; heterocyclic; substituted heterocyclic; trifluoromethyl; halogen; cyano; nitro; $S(O)Y^1$, $S(O)_2Y^1$, $S(O)_2OY'$ or $S(O)_2NHY^1$, wherein each $Y^1$ is independently hydrogen, lower alkyl, alkenyl, alkynyl or aryl, with the proviso that when $R^3$, $R^4$ or $R^5$ is $S(O)Y^1$, $Y^1$ is not hydrogen, and with the further proviso that when $Y^1$ is alkenyl or alkynyl, the site of unsaturation is not conjugated with a heteroatom; $C(O)Y^2$, wherein $Y^2$ is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, with the proviso that the carbonyl functionality is not conjugated with an alkenyl or alkynyl functionality; $OY^3$ or $N(Y^3)_2$ wherein each $Y^3$ is independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, acyl, trifluoromethyl, alkylsulfonyl or arylsulfonyl, with the proviso that $OY^3$ or $N(Y_3)_2$ functionality is not conjugated with an alkenyl or alkynyl functionality; $SY^4$ wherein $Y^4$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, with the proviso that the $SY^4$ functionality is not conjugated with an alkenyl or alkynyl functionality; or $R^3$ and $R^4$ together form a three to eight membered saturated or unsaturated ring, wherein from one to three carbon atoms of said ring may optionally and independently be replaced by a nitrogen, oxygen or sulfur atom, and wherein said rings may optionally be substituted with one or more substituents that are defined as $Z^3$ and $Z^4$; or either $Z^1$ and $Z^2$ or $Z^1$ and $Z^3$ together form a fused ring structure; or either $Z^2$ and $Z^4$ $Z^3$ and $Z^4$ together form a spiro ring structure;

$R^5$ is selected from the group consisting of alkyl; substituted alkyl; cycloalkyl; substituted cycloalkyl; alkenyl; substituted alkenyl; alkynyl; substituted alkynyl; aryl; substituted aryl; arylalkyl; substituted arylalkyl; arylalkenyl; substituted arylalkenyl; arylalkynyl; substituted arylalkynyl; heterocyclic; substituted heterocyclic; $S(O)Y^{1'}$, $S(O)_2Y^1$, $S(O)^2OY^1$ or $S(O)_2NHY^1$, wherein each $Y^1$ is independently hydrogen, lower alkyl, alkenyl, alkynyl or aryl, with the proviso that when $R^3$, $R^4$ or $R^5$ is $S(O)Y^1$, $Y^1$ is not hydrogen, and further with the proviso that when $Y^1$ is alkenyl or alkynyl, the site of unsaturation is not conjugated with a heteroatom; $C(O)Y^2$, wherein $Y^2$ is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, with the proviso that the carbonyl functionality is not conjugated with an alkenyl or alkynyl functionality; $OY^3$ or $N(Y^3)_2$ wherein each $Y^3$ is independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, acyl, trifluoromethyl, alkylsulfonyl or arylsulfonyl, with the proviso that the $OY^3$ or $N(Y^3)_2$ functionality is not conjugated with an alkenyl or alkynyl functionality; $SY^4$ wherein $Y^4$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, with the proviso that the $SY^4$ functionality is not conjugated with an alkenyl or alkynyl functionality; and with the further proviso that when A and B are carbon, $R^5$ is not N-alkyl or branched alkyl with 2–19 carbon atoms, cycloalkyl, aralkyl, N-alkenyl or alkenyl with 2–19 carbon atoms, or N-alkynyl or branched alkynyl with 2 to 19 carbon atoms;

$R^6$ is hydrogen;

X is selected from the group consisting of Cl, Br, I, $HSO_4$, $½SO_2$, $CH_3SO_3$, p-TsO and $CF_3SO_3$; and Y is selected from the group consisting of 2Cl, 2Br, 2I, $2HSO_4$, $SO_2$, $2CH_3SO_3$, 2p-TsO and $2CF_3SO_3$.

When $R^3$ and $R^4$ together form a three to eight membered saturated or unsaturated ring or either $^1$ and $Z^2$ or $^1$ and $Z^3$ together form a fused ring structure, the fused ring or saturated or unsaturated ring selected from the group consisting of benzene, pyridine, pyran, indene, isoindene, benzofuran, isobenzofuran, benzo[b]thiophene, benzo[c]thiophene, indole, indolenine, isoindole, cyclopental[b]pyridine, pyrano[3,4-b]pyrrole, indazole, indoxazine, benzosazole, anthranil, naphthalene, tetralin, decalin, chromene, coumarin, chroman-4-one, isocoumarin, isochromen-3-one, quinoline, isoquinoline, cinnoline, quinazoline, naphthyridine, pyrido[3,4-b]-pyridine, pyridol[3,2-b]pyridine, pyrido[4,3-b]-pyridine, benzoxazine, anthracene, phenanthrene, phenalene, fluorene, carazole, xanthene, acridine, octahydro-[1]pyridine, 1-methyl octahydro-[1]pyridine, octahydro-indole, 1-methyl octahydro-indole, octahydro-cyclopenta[b]pyrrole, 1-methyl-octahydrocyclopenta[b]pyrrole, decahydro-quinoline, and 1-methyl-decahydroquinoline.

It is preferred that Q is either $CH_2$, $CH_2CH_2$, $CH=CH—$, $C(CH_3)=CH$, $CH=C(CH_3)$, or $C(CH_3)=C(CH_3)$; A and B are each carbon; $R^1$ is a $C_1-C_{10}$ alkyl or more preferably a $C_1-C_6$ alkyl alkyl or even more preferably a $C_1-C_4$ alkyl such as methyl, ethyl, isopropyl or isobutyl; $R^2$ is hydrogen; $R^3$ and $R^4$ are individually selected from the group consisting of hydrogen, halogen, alkyl or alkanoyl; $R^5$ is a branched or non-branched $C_4-C_{19}$ alkyl, cycloalkyl, alkenyl, alkynyl, aryl, arylalkyl arylalkenyl, arylalknyl; $Z^1$, $Z^2$, $Z^3$ and $Z_4$ are each hydrogen, or $Z^3$ and $Z_4$ are hydrogen, $Z^1$ and $Z^2$ and their associated carbon atoms combine to form a five or six membered fused ring structure, or $Z^2$ and $Z^4$ are hydrogen, $Z^1$ and $Z^3$ and their associated carbon atoms combine to form a five or six membered fused ring structure, or $Z^1$ and $Z^3$ are hydrogen, $Z^2$ and $Z^4$ and their associated carbon atoms combine to form a five or six membered spiro ring structure, or $Z^1$ and $Z^2$ are hydrogen, $Z^3$ and $Z^4$ and their associated carbon atoms combine to form a five or six membered spiro ring structure; and X is iodine or bromine.

As employed herein, the meaning of the aforementioned terms are defined as follows:

"lower alkyl" refers to straight or branched chain alkyl radicals having in the range of about 1 up to 4 carbon atoms;

"alkyl" refers to straight or branched chain alkyl radicals having in the range of about 1 up to 19 carbon atoms and "substituted alkyl" refers to alkyl radicals further bearing one or more substituents such as hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, sulfonamide, and the like.

"cycloalkyl" refers to cyclic ring-containing moieties containing in the range of about 3 up to 8 carbon atoms and "substituted cycloalkyl" refers to cycloalkyl moieties further bearing one or more substituent as set forth above;

"alkenyl" refers to straight or branched chain hydrocarbyl groups having at least one carbon-carbon double bond, and having in the range of about 2 up to 19 carbon atoms and "substituted alkenyl" refers to alkenyl groups further bearing one or more substituents as set forth above;

"alkynyl" refers to straight or branched chain hydrocarbyl moieties having at least one carbon-carbon triple bond, and having in the range of about 2 up to 19 carbon atoms and "substituted alkynyl" refers to alkynyl moieties further bearing one or more substituents as set forth above;

"aryl" refers to aromatic groups having in the range of 6 up to 24 carbon atoms and "substituted aryl" refers to aryl groups further bearing one or more substituents as set forth above;

"alkylaryl" refers to alkyl-substituted aryl groups and "substituted alkylaryl" refers to alkylaryl groups further bearing one or more substituents as set forth above;

"arylalkyl" refers to aryl-substituted alkyl groups and "substituted arylalkyl" refers to arylalkyl groups further bearing one or more substituents as set forth above;

"arylalkenyl" refers to aryl-substituted alkenyl groups and "substituted arylalkenyl" refers to arylalkenyl groups further bearing one or more substituents as set forth above; "arylalkynyl" refers to aryl-substituted alkynyl groups and "substituted arylalkynyl" refers to arylalkynyl groups further bearing one or more substituents as set forth above;

"aroyl" refers to aryl-substituted species such as benzoyl and "substituted aroyl" refers to aroyl moieties further bearing one or more substituents as set forth above;

"heterocyclic" refers to cyclic moieties containing one or more heteroatoms as part of the ring structure, and having in the range of 3 up to 24 carbon atoms and "substituted heterocyclic"refers to heterocyclic moieties further bearing one or more substituents as set forth above; "acyl" refers to alkyl-carbonyl species;

"halogen" refers to fluoride, chloride, bromide or iodide groups.

Examples of pharmaceutically acceptable salts include inorganic and organic acid addition salts such as hydrochloride, hydrobromide, nitrate, sulfate, phosphate, acetate, methanesulfonate, p-toluenesulfonate, benzenesulfonate, salicylate, propionate, ascorbate, aspartate, fumarate, galactarate, maleate, citrate, glutamate, glycolate, lactate, malate, maleate, tarrate, oxalate, succinate, or similar pharmaceutically-acceptable inorganic or organic acid addition salts, and include the pharmaceutically acceptable salts listed in the *Journal of Pharmaceutical Science*, 66, 2. (1977) which are hereby incorporated by reference. The above salt forms may be in some cases hydrates or solvates with alcohols and other solvents.

When used in reference to compounds of the invention, "an effective amount" refers to doses of compound sufficient to provide circulating concentrations high enough to impart a beneficial effect on the recipient thereof for alleviating a disease or pathological symptom of a CNS pathology. The amount to be administered depends to some extent on the lipophilicity of the specific compound selected, since it is expected that this property of the compound will cause it to partition into fat deposits of the subject. The precise amount to be administered can be determined by the skilled practitioner in view of desired dosages, side effects and medical history of the patient and the like. It is anticipated that the compound will be administered in the amount ranging $1 \times 10^{-5}$ to about 100 mg/kg/day, with amounts in the range of about $1 \times 10^{-2}$ up to 1 mg/kg/day being preferred.

A pharmaceutical composition containing a compound of the invention is also contemplated, which may include a conventional additive, such as a stabilizer, buffer, salt, preservative, filler, flavor enhancer and the like, as known to those skilled in the art. Representative buffers include phosphates, carbonates, citrates and the like. Exemplary preservatives include EDTA, EGTA, BHA, BHT and the like. A composition of the invention may be administered by inhalation, i.e., intranasally as an aerosol or nasal formulation; topically, i.e., in the form of an ointment, cream or lotion; orally, i.e., in solid or liquid form (tablet, gel cap, time release capsule, powder, solution, or suspension in aqueous or non aqueous liquid; intravenously as an infision or injection, i.e., as a solution, suspension or emulsion in a pharmaceutically acceptable carrier, transdermally, e.g., via a transdermal patch; rectally as a suppository and the like.

The present invention includes all possible diastereomers and all enantiomeric forms as well as racemic mixtures. The compounds can be separated into substantially optically pure compounds. The compounds of the invention are nicotinic receptor agents. They inhibit [$^3$H]NIC binding and [$^3$H] MLA binding and NIC-evoked [$^3$H]DA release.

Examples of compounds falling within the scope of the present invention precede the appended claims. If one specific enantiomer is shown or described, the other enantiomer may readily be made from the appropriate chiral precursor or can be resolved from a racemic mixture.

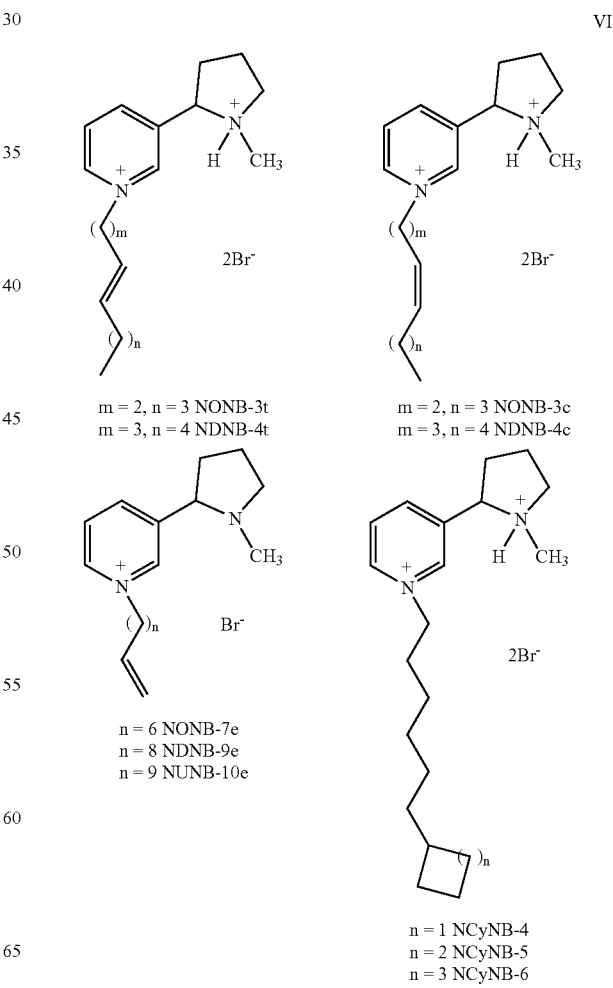

VI

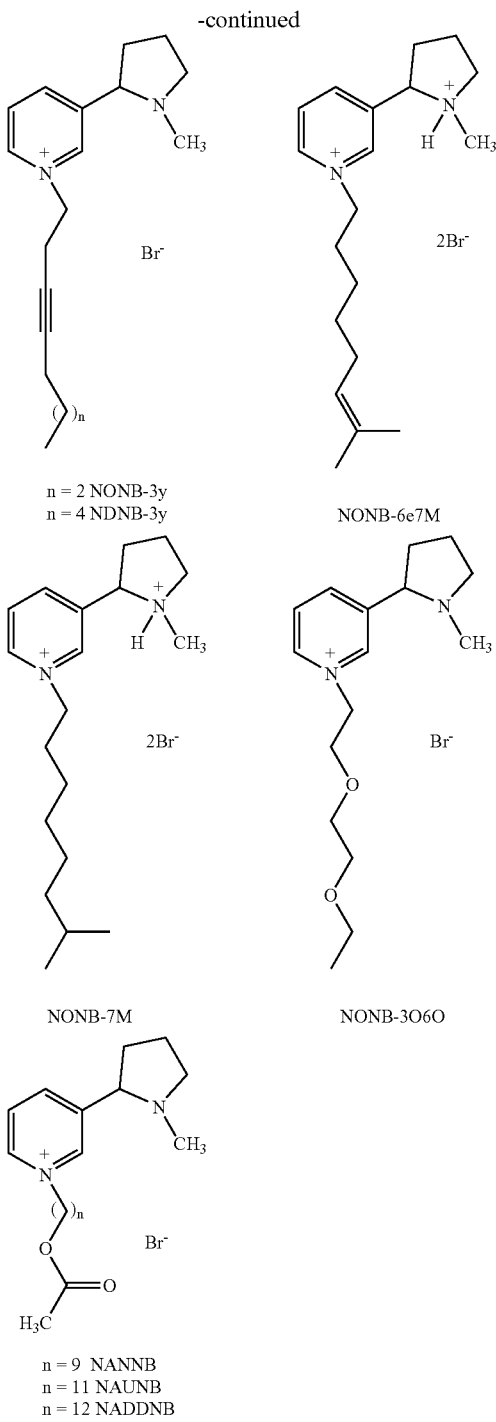

n = 2 NONB-3y
n = 4 NDNB-3y

NONB-6e7M

NONB-7M

NONB-3O6O n = 9 NANNB
n = 11 NAUNB
n = 12 NADDNB (S)-trans-3-(1-Methyl-pyrolidin-2-yl)-1-oct-3-enyl-pyridu-ium bromide hydrobromide salt (NONB-3t);
(S)-trans-1-Dec-4-enyl-3(1methyl-pyrrolidin-2-yl)-pyridinium bromide (NDNB-4t);
(S)-cis-3-(1-Methyl-pyrrolidin-2-yl)-1-oct-3-enyl-pyridinium bromide hydrobromide salt (NONB-3c);
(S)-cis-1-Dec-4-enyl-3-(1-methyl-pyrrolidin-2-yl)-pyridinium bromide hydrobromide salt (NDNB-4c);
(S)-3-(1-Methyl-pyrrolidin-2-yl)-1-oct-7-enyl -pyridinium bromide (NONB-7e);
(S)-1-Dec-9-enyl-3-(1-methyl-pyrrolidin-2-yl)-pyridinium bromide (NDNB-9e);
(S)-3-(1-Methyl-pynolidin-2-yl)-1-undec-10-enyl-pyridinium bromide (NUNB-10e);
(S)-1-(6-Cyclobutyl-hexyl)3-(1-methyl-pyrrolidin-2-yl)-pyridinium bromide hydrobromide salt (NCyNB-4);
(S)-1-(6-Cyclopentyl-hexyl)-3-(1-methyl-pyrrolidin-2-yl)-pyridinium bromide hydrobromide salt (NCyNB-5);
(S)-1-(6-Cyclohexyl-hexyl)-3-(1-methyl-pyrrolidin-2-yl)-pyridmium bromide hydrobromide salt (NCyNB-6);
(S)-3-(1-Methyl-pyrrolidin-2-yl)-1-oct-3-ynyl-pyridinium bromide (NONB-3y);
(S)-1-Dec-3-ynyl-3-(1-methyl-pyrrolidin-2-yl)pyridinium bromide (NDNB-3y);
(S)-1-(7-Methyl-oct-6-enyl)-3-(1-methyl-pyrrolidin-2-yl)-pyridinium bromide hydrobrormide (NONB-6e7M);
(S)-1-(7-Methyl-octyl)-3-(1-methyl-pyrrolidin-2-yl)-pyridinium bromide hydrobromide salt (NONB-7M);
(S)-1-[2-(2-Ethoxy-ethoxy)-ethyl]-3-(1-methyl-pyrrolidin-2-yl)-pyridinium bromide (NONB-3O6O);
(S)-1-(9-Acetoxy-nonyl)-3-(1-methyl-pyrrolidin-2-yl)-pyridinium bromide (NANNB);
(S)-1-(11-Acetoxy-undecyl)-3-(1-methyl-pyrrolidin-2-yl)-pyridinium bromide (NAUNB);
(S)-1-(12-Acetoxy-dodecyl)-3-(1-methyl-pyrrolidin-2-yl)-pyridinium bromide (NADDNB);

These compounds can be prepared from corresponding free bases by reaction with an appropriate alkyl iodide using techniques known to those skilled in the art of organic synthesis.

The invention will now be described in greater detail by reference to the following non-limiting examples.

EXAMPLE 1

(S)-trans-3-(1-Methyl-pyrrolidin-2-yl)-1-oct-3-enyl-pyridinium bromide hydrobromide salt (NONB-3t)

1a. trans-Oct-3-en-1-ol

A solution of oct-3-yn-1-ol (2.52 g, 20.0 mmol), t-BuOH (5 g), THF (10 mL) and liquid $NH_3$ was cooled to −36° C. Pieces of Lithium (0.34 g, 50 mmol) were introduced with vigorous stirrng and maintaining the temperature. After 2 h, $NH_3$ was allowed to evaporate overnight. Saturated $NH_4Cl$ solution was added and the reaction mixture was extracted with hexane. The combined organic layers were washed with 1 M HCl, aqueous $NaHCO_3$ and brine successively and dried. Evaporation of the solvent gave trans-oct-3-en-1-ol (2.44 g, 95%) as a pale yellow oil, which was used in the next step without further purification: $^1H$ NMR (300 MHz, $CDCl_3$) δ 5.54 (1H, m), 5.36 (1H, m), 3.66 (2H, t, J=6.3 Hz), 2.25 (2H, m), 2.02 (2H, m), 1.74 (1H, br s), 1.31 (4H, m), 0.88 (3H, t, J=7.2 Hz); $^{13}C$ NMR (75 MHz, $CDCl_3$) δ 134.27, 125.78, 62.22, 36.22, 32.59, 31.86, 22.47, 14.20.

1b. trans-1-Bromo-oct-3-ene

To a solution of trans-oct-3-en-1-ol (1.28 g, 10.0 mmol) in DMF (25 mL) was added triphenylphosphine (2.92 g, 11.1 mmol). The solution was cooled to 0° C. and NBS (1.92 g, 10.8 mmol) was added in portions. After stirring for 30 min at room temperature, the reaction was quenched with methanol (1 mL). The solution was diluted with ether (100 mL), washed with water, saturated aqueous $NaHCO_3$ and brine successively. The organic layer was dried and concentrated. The residue was purified by flash chromatography on silica gel, eluting with hexane to afford trans-1-bromo-oct-3-ene (1.40 g, 73%) as a colorless oil: $^1H$ NMR (300 MHz, $CDCl_3$) δ 5.54 (1H, m), 5.39 (1H, m), 3.37 (2H, t, J=7.2 Hz), 2.54 (2H, m), 2.02 (2H, m) 1.34 (4H, m), 0.89 (3H, t, J=7.2 Hz); $^{13}$C NMR (75 MHz, CDCl$_3$) δ 134.09, 126.45, 36.34, 33.21, 32.48, 31.73, 22.45, 14.24.

1c. (S)-trans-3-(1-Methyl-pyrrolidin-2-yl)-1-oct-3enyl-pyridinium bromide hydrobromide salt (NONB-3t)

To a stirred solution of (S)-nicotine (0.46 g, 2.8 mmol) in AcOH (10 ml) was added trans-1-bromo-oct-3-ene (1.37 g, 7.17 mmol). The mixture was heated at reflux for 3 days. AcOH was evaporated and the residue was recrystallized in ethyl acetate-CHCl$_3$ to afford (S)-trans-3-(1-methyl-pyrrolidin-2-yl)-1-oct-3-enyl-pyridinium bromide hydrobromide salt (NONB-3t) (0.76 g, 62%) as hygroscopic white crystals: $^1$H NMR (300 MHz, CDCl$_3$) δ 11.55 (1H, s), 10.27 (1H, s), 9.46 (1H, d, J=7.5 Hz), 9.16 (1H, d, J=5.7 Hz), 8.22 (1H, dd, J=7.5, 5.7 Hz), 5.72 (1H, m), 5.41 (2H, m), 4.88 (2H, m), 3.98 (1H, m), 3.38 (1H, m), 2.94 (3H, s), 2.60–2.90 (3H, m), 2.43 (3H, m), 1.86 (2H, m), 1.00–1.25 (4H, m), 0.79 (3H, t, J=7.2 Hz); $^{13}$C NMR (75 MHz, CDCl$_3$) δ 147.29, 146.41, 145.11, 137.58, 134.31, 128.44, 122.37, 67.18, 62.27, 56.04, 38.57, 34.49, 32.30, 32.00, 31.41, 22.32, 21.83, 14.12; Anal. Calcd for C$_{18}$H$_{30}$Br$_2$N$_2$.0.3H$_2$O: C, 49.22; H, 6.93; N, 6.38. Found: C, 49.25; H, 7.03; N, 6.30.

EXAMPLE 2

(S)-trans-1-Dec-4-enyl-3-(1-methyl-pyrrolidin-2-yl)-pyridinium bromide (NDNB-4t)

2a. trans-Dec-4-en-1-ol

Sodium borohydride (0.60 g, 3.8 mmol) was added in portions to a stirred solution of trans-dec-4-enal (1.54 g, 10.0 mmol) in methanol (50 mL). The reaction was stirred at room temperature for 30 min followed by the addition of saturated NH$_4$Cl. Methanol was evaporated and water was added to the residue. The mixture was extracted with ether and the combined organic layers were washed with water and dried. Evaporation of the solvent gave trans-dec-4-en-1-ol (1.52 g, 97%) as a pale yellow oil, which was used in the next step without further purification: $^1$H NMR (300 MHz, CDCl$_3$) δ 5.39 (2H, m), 3.60 (2H, t, J=6.6 Hz), 2.02 (5H, m), 1.56 (2H, m), 1.23 (6H, m), 0.84 (3H, t, J=6.9 Hz); $^{13}$C NMR (75 MHz, CDCl$_3$) δ 131.31, 129.44, 62.66, 32.80, 32.70, 31.67, 29.51, 29.18, 22.82, 14.36.

2b. trans-1-Bromo-dec-4-ene

To a solution of trans-dec-4-en-1-ol (1.52 g, 9.74 mmol) in DMF (25 mL) was added triphenylphosphine (2.81 g, 10.7 mmol). The solution was cooled to 0° C. and NBS (1.85 g, 10.4 mmol) was added in portions. After stirring for 30 min at room temperature, the reaction was quenched with methanol (1 mL). The solution was diluted with ether (100 mL), washed with water, saturated aqueous NaHCO$_3$ and brine successively. The organic layer was dried and concentrated. The residue was purified by flash chromatography on silica gel, eluting with hexane to afford trans-1-bromo-dec-4-ene (1.60 g, 75%) as a colorless oil: $^1$H NMR (300 MHz, CDCl$_3$) δ 5.49 (1H, m), 5.35 (1H, m), 3.42 (2H, t, J=6.6 Hz), 2.15 (2H, m), 1.96 (4H, m), 1.29 (6H, m), 0.90 (3H, t, J=7.2 Hz); $^{13}$C NMR (75 MHz, CDCl$_3$) δ 132.36, 127.89, 33.61, 32.80, 32.73, 31.65, 31.14, 29.45, 22.82, 14.36.

2c. (S)-trans-1-Dec-4-enyl-3-(1-methyl-pyrrolidin-2-yl)-pyridinium bromide (NDNB-4t)

To a stirred solution of (S)-nicotine (0.47 g, 2.9 mmol) in AcOH (15 ml) was added trans-1-bromo-dec-4-ene (1.55 g, 7.08 mmol). The mixture was heated at reflux for 3 days. AcOH was evaporated and the residue was dissolved in CHCl$_3$. The mixture was washed with saturated aqueous NaHCO$_3$, water and brine successively and dried. Evaporation of the solvent followed by titration with ether afforded 0.82 g (74%) of (S)-trans-1-dec-4-enyl-3-(1-methyl-pyrrolidin-2-yl)-1-pyridinium bromide (NDNB-4t) as a brown oil. $^1$H NMR (300 MHz, CDCl$_3$) δ 9.71 (1H, d, J=5.7 Hz), 9.07 (1H, s), 8.40 (1H, d, J=8.1 Hz), 8.08 (1H, dd, J=8.1, 6.0 Hz), 5.42 (2H, m), 5.00 (2H, t, J=6.9 Hz), 3.54 (1H, t, J=8.4 Hz), 3.25 (1H, m), 2.44 (2H, m), 2.25 (3H, s), 1.65–2.20 (8H, m), 1.66 (1H, m), 1.15–1.40 (6H, m), 0.87 (3H, t, J=7.2 Hz); $^{13}$C NMR (75 MHz, CDCl$_3$) δ 146.50, 144.36, 143.79, 143.13, 128.52, 127.15, 67.05, 61.49, 56.86, 40.70, 36.07, 32.67, 31.76, 31.56, 29.27, 29.07, 23.39, 22.70, 14.27; Anal. Calcd for C$_{20}$H$_{33}$BrN$_2$.0.3H$_2$O: C, 62.10; H, 8.76; N, 7.24. Found: C, 62.03; H, 8.88; N, 7.12.

EXAMPLE 3

(S)-cis-3-(1-Methyl-pyrrolidin-2-yl)-1-oct-3-enyl-pyridinium bromide hydrobromide salt (NONB-3c)

3a. cis-1-Bromo-oct-3-ene

To a solution of cis-oct-3-en-1-ol (1.00 g, 7.81 mmol) in DMF (18 mL) was added triphenylphosphine (2.28 g, 8.69 mmol). The solution was cooled to 0° C. and NBS (1.50 g, 8.43 mmol) was added in portions. After stirring for 30 min at room temperature, the reaction was quenched with methanol (1 mL). The solution was diluted with ether (100 mL), washed with water, saturated aqueous NaHCO$_3$ and brine successively. The organic layer was dried and concentrated. The residue was purified by flash chromatography on silica gel, eluting with hexane to afford cis-1-bromo-oct-3-ene (1.36 g, 91%) as a colorless oil: $^1$H NMR (300 MHz, CDCl$_3$) δ 5.53 (1H, m), 5.35 (1H, m), 3.36 (2H, t, J=7.2 Hz), 2.60 (2H, m), 2.04 (2H, m), 1.33 (4H, m), 0.89 (3H, t, J=7.2 Hz); $^{13}$C NMR (75 MHz, CDCl$_3$) δ 133.27, 125.84, 32.93, 31.97, 31.12, 27.43, 22.64, 14.30.

3b. (S)-cis-3-(1-Methyl-pyrrolidin-2-yl)-1-oct-3-enyl-pyridinium bromide hydrobromide salt (NONB-3c)

To a stirred solution of (S)-nicotine (0.47 g, 2.9 mmol) in AcOH (8 ml) was added cis-1-bromo-oct-3-ene (1.34 g, 7.00 mmol). The mixture was heated at reflux for 3 days. AcOH was evaporated and the residue was recrystallized in ethyl acetate-CHCl$_3$ to afford (S)-cis-3-(1-methyl-pyrrolidin-2-yl)-1-oct-3-enyl-pyridinium bromide hydrobromide salt (NONB-3c) (0.62 g, 49%) as hygroscopic white crystals: $^1$H NMR (300 MHz, CDCl$_3$) δ 12.19 (1H, s), 10.71 (1H, s), 9.74 (1H, d, J=7.8 Hz), 8.74 (1H, d, J=5.7 Hz), 8.16 (1H, dd, J=7.8, 5.7 Hz), 5.79 (1H, m), 5.58 (1H, m), 5.40 (1H, m), 4.82 (2H, m), 4.01 (1H, m), 3.03 (1H, m), 2.94 (3H, d, J=4.2 Hz), 2.20–2.90 (5H, m), 1.87 (1H, m), 1.70 (2H, m), 1.00–1.25 (4H, m), 0.79 (3H, t, J=7.2 Hz); $^{13}$C NMR (75 MHz, CDCl$_3$) δ 146.96, 146.29, 145.29, 136.33, 134.12, 128.37, 121.81, 67.09, 62.01, 55.92, 38.53, 31.94, 31.41, 29.34, 26.94, 22.18, 21.72, 14.04; Anal. Calcd for C$_{18}$H$_{30}$Br$_2$N$_2$.0.4H$_2$O: C, 48.97; H, 7.03; N, 6.35. Found: C, 49.00; H, 7.36; N, 6.39.

EXAMPLE 4

(S)-cis-1-Dec-4-enyl-3-(1-methyl-pyrrolidin-2-yl)-pyridinium bromide hydrobromide salt (NDNB-4c)

4a. cis-1-Bromo-dec-4-ene

To a solution of cis-dec-4-en-1-ol (1.00 g, 6.41 mmol) in DMF (15 mL) was added triphenylphosphine (1.87 g, 7.13 mmol). The solution was cooled to 0° C. and NBS (1.23 g, 6.91 mmol) was added in portions. After stirring for 30 min at room temperature, the reaction was quenched with methanol (0.6 mL). The solution was diluted with ether (60 mL), washed with water, saturated aqueous NaHCO₃ and brine successively. The organic layer was dried and concentrated. The residue was purified by flash chromatography on silica gel, eluting with hexane to afford cis-1-bromo-dec-4-ene (1.23 g, 96%) as a colorless oil: $^1$H NMR (300 MHz, CDCl₃) δ 5.38 (1H, m), 5.29 (1H, m), 3.39 (2H, t, J=6.9 Hz), 2.17 (2H, m), 2.03 (2H, m), 1.88 (2H, m), 1.28 (6H, m), 0.87 (3H, t, J=6.6 Hz); $^{13}$C NMR (75 MHz, CDCl₃) δ 131.87, 127.39, 33.65, 32.90, 31.76, 29.63, 27.51, 25.87, 22.83, 14.35.

4b. (S)-cis-1-Dec-4-enyl-3-(1-methyl-pyrrolidin-2-yl)-pyridinium bromide hydrobromide salt (NDNB-4c)

To a stirred solution of (S)-nicotine (0.35 g, 2.2 mmol) in AcOH (10 ml) was added cis-1-bromo-dec-4-ene (1.15 g, 5.25 mmol). The mixture was heated at reflux for 3 days. AcOH was evaporated and the residue was recrystallized in ethyl acetate-CHCl₃ to afford (S)-cis-1-dec-4-enyl-3-(1-methyl-pyrrolidin-2-yl)-pyridinium bromide hydrobromide salt (NDNB-4c) (0.54 g, 54%) as hygroscopic white crystals: $^1$H NMR (300 MHz, CDCl₃) δ 11.93 (1H, s), 10.75 (1H, s), 9.78 (1H, d, J=7.8 Hz), 8.69 (1H, d, J=6.0 Hz), 8.20 (1H, dd, J=7.8, 6.0 Hz), 5.88 (1H, m), 5.49 (1H, m), 5.30 (1H, m), 4.72 (2H, m), 4.01 (1H, m), 3.30 (1H, m), 2.97 (3H, d, J=5.1 Hz), 2.73 (1H, m), 2.10–2.60 (7H, m), 1.96 (2H, m), 1.70 (2H, m), 1.15–1.40 (6H, m), 0.86 (3H, t, J=7.2 Hz); $^{13}$C NMR (75 MHz, CDCl₃) δ 147.41, 146.38, 144.98, 134.68, 132.93, 128.93, 126.06, 67.20, 62.37, 56.07, 38.71, 32.00, 31.64, 31.38, 29.34, 27.61, 23.94, 22.74, 21.91, 14.32; Anal. Calcd for C₂₀H₃₄Br₂N₂.0.5H₂O: C, 50.97; H, 7.49; N, 5.94. Found: C, 50.90; H, 7.55; N, 5.94.

EXAMPLE 5

(S)-3-(1-Methyl-pyrrolidin-2-yl)-1-oct-7-enyl-pyridinium bromide (NONB-7e)

To a stirred solution of (S)-nicotine (0.12 g, 0.71 mmol) in AcOH (2 ml) was added 8-bromo-oct-1-ene (0.34 g, 1.8 mmol). The mixture was heated at reflux for 3 days. AcOH was evaporated and the residue was dissolved in CHCl₃. The mixture was washed with saturated aqueous NaHCO₃, water and brine successively and dried. Evaporation of the solvent followed by titration with ether afforded 0.19 g (77%) of (S)-3-(1-methyl-pyrrolidin-2-yl)-1-oct-7-enyl-pyridinium bromide (NONB-7e) as a brown oil. $^1$H NMR (300 MHz, CDCl₃) δ 9.70 (1H, d, J=6.0 Hz), 9.21 (1H, s), 8.41 (1H, d, J=8.1 Hz), 8.08 (1H, dd, J=8.1, 6.0 Hz), 5.72 (1H, m), 4.86–5.10 (4H, m), 3.50 (1H, t, J=8.4 Hz), 3.22 (1H, m), 2.41 (2H, m), 2.20 (3H, s), 1.80–2.10 (6H, m), 1.61 (1H, m), 1.20–1.44 (6H, m); $^{13}$C NMR (75 MHz, CDCl₃) δ 146.12, 144.00, 143.28, 142.63, 138.22, 128.05, 114.20, 66.68, 61.67, 56.48, 40.29, 35.67, 33.30, 31.88, 28.33, 28.27, 25.76, 22.98; Anal. Calcd for C₁₈H₂₉BrN₂.0.35HBr: C, 56.65; H, 7.75; N, 7.34. Found: C, 56.96; H, 7.98; N, 6.95.

EXAMPLE 6

(S)-1-Dec-9-enyl-3-(1-methyl-pyrrolidin-2-yl)-pyridinium bromide (NDNB-9e)

6a. 10-Bromo-dec-1-ene

To a solution of dec-9-en-1-ol (1.22 g, 7.82 mmol) in DMF (18 mL) was added triphenylphosphine (2.30 g, 8.77 mmol). The solution was cooled to 0° C. and NBS (1.52 g, 8.54 mmol) was added in portions. After stirring for 30 min at room temperature, the reaction was quenched with methanol (0.8 mL). The solution was diluted with ether (80 mL), washed with water, saturated aqueous NaHCO₃ and brine successively. The organic layer was dried and concentrated. The residue was purified by flash chromatography on silica gel, eluting with hexane to afford 10-bromo-dec-1-ene (1.38 g, 81%) as a colorless oil: $^1$H NMR (300 MHz, CDCl₃) δ 5.80 (1H, m), 4.94 (2H, m), 3.38 (2H, t, J=6.9 Hz), 2.02 (2H, m), 1.83 (2H, m), 1.20–1.55 (10H, m); $^{13}$C NMR (75 MHz, CDCl₃) δ 139.17, 114.30, 34.29, 34.02, 33.06, 29.53, 29.25, 29.12, 28.96, 28.40.

6b. (S)-1-Dec-9-enyl-3-(1-methyl-pyrrolidin-2-yl)-pyridinium bromide (NDNB-9e)

To a stirred solution of (S)-nicotine (0.52 g, 3.2 mmol) in AcOH (10 ml) was added 10-bromo-dec-1-ene (1.66 g, 7.58 mmol). The mixture was heated at reflux for 3 days. AcOH was evaporated and the residue was dissolved in CHCl₃. The mixture was washed with saturated aqueous NaHCO₃, water and brine successively and dried. Evaporation of the solvent followed by titration with ether afforded 0.74 g (61%) of (S)-1-dec-9-enyl-3-(1-methyl-pyrrolidin-2-yl)-pyridinium bromide (NDNB-9e) as a brown oil. $^1$H NMR (300 MHz, CDCl₃) δ 9.65 (1H, d, J=5.1 Hz), 9.14 (1H, s), 8.41(1H, d, J=8.1 Hz), 8.09 (1H, dd, J=8.1, 5.1 Hz), 5.75 (1H, m), 4.88–5.10 (4H, m), 3.54 (1H, t, J=8.1 Hz), 3.23 (1H, m), 2.45 (2H, m), 2.22 (3H, s), 1.70–2.10 (6H, m), 1.61 (1H, m), 1.10–1.40 (10H, m); $^{13}$C NMR (75 MHz, CDCl₃) δ 146.46, 144.39, 143.74, 142.97, 139.07, 128.50, 114.33, 67.17, 62.25, 56.92, 40.74, 36.11, 33.93, 32.35, 29.42, 29.24, 29.15, 29.03, 26.35, 23.41.

EXAMPLE 7

(S)-3-(1-Methyl-pyrrolidin-2-yl)-1-undec-10-enyl-pyridinium bromide (NUNB-10e)

7a. Undec-10-en-1-ol

A mixture of undec-10-yn-1-ol (0.84 g, 5.0 mmol), quinoline (0.13 ml), Lindlar's catalyst (100 mg, 17% w/w) and EtOH (20 mL) was hydrogenated in a Parr apparatus at 50 psi of H₂ for 1 h. The mixture was filtered through Celite, and the filtrate was concentrated in vacuo to dryness to give undec-10-en-1-ol (0.86 g, 100%) as a colorless oil, which was used in the next step without further purification: $^1$H NMR (300 MHz, CDCl₃) δ 5.78 (1H, m), 4.92 (2H, m), 3.61 (2H, t, J=6.6 Hz), 2.01 (2H, m), 1.53 (3H, m), 1.21–1.40 (12H, m); $^{13}$C NMR (75 MHz, CDCl₃) δ 139.43, 114.31, 63.24, 34.00, 32.98, 29.74, 29.61, 29.31, 29.11, 25.92.

7b. 11-Bromo-undec-1-ene

To a solution of undec-10-en-1-ol (0.86 g, 5.0 mmol) in DMF (15 mL) was added triphenylphosphine (1.46 g, 5.6 mmol). The solution was cooled to 0° C. and NBS (0.96 g, 5.4 mmol) was added in portions. After stirring for 30 min at room temperature, the reaction was quenched with methanol (0.5 mL). The solution was diluted with ether (80 mL), washed with water, saturated aqueous NaHCO₃ and brine successively. The organic layer was dried and concentrated. The residue was purified by flash chromatography on silica gel, eluting with hexane to afford 11-bromo-undec-1-ene (0.96 g, 82%) as a colorless oil: $^1$H NMR (300 MHz, CDCl₃) δ 5.79 (1H, m), 4.93 (2H, m), 3.38 (2H, t, J=6.9 Hz), 2.02 (2H, m), 1.83 (2H, m), 1.20–1.55 (12H, m); $^{13}$C NMR (75 MHz, CDCl₃) δ 139.36, 114.33, 34.27, 33.99, 33.01, 29.57×2, 29.27, 29.09, 28.94, 28.35.

7c. (S)-3-(1-Methyl-pyrrolidin-2-yl)-1-undec-10-enyl-pyridinium bromide (NUNB-10e)

To a stirred solution of (S)-nicotine (0.14 g, 0.86 mmol) in AcOH (4 ml) was added 11-bromo-undec-1-ene (0.50 g, 2.1 mmol). The mixture was heated at reflux for 3 days. AcOH was evaporated and the residue was dissolved in CHCl₃. The mixture was washed with saturated aqueous NaHCO$_3$, water and brine successively and dried. Evaporation of the solvent followed by titration with ether afforded 0.22 g (67%) of (S)-3-(1-methyl-pyrrolidin-2-yl)-1-undec-10-enyl-pyridinium bromide (NUNB-10e) as a brown oil. $^1$H NMR (300 Mz, CDCl$_3$) δ 9.61 (1H, d, J=5.7 Hz), 9.22 (1H, s), 8.40 (1H, d, J=8.1 Hz), 8.08 (1H, dd, J=8.1, 6.0 Hz), 5.77 (1H, m), 4.85–5.10 (4H, m), 3.54 (1H, t, J=8.1 Hz), 3.24 (1H, m), 2.43 (2H, m), 2.23 (3H, s), 1.80–2.15 (6H, m), 1.63 (1H, m), 1.10–1.44 (12H, m); $^{13}$C NMR (75 MHz, CDCl$_3$) δ 146.43, 144.21, 143.65, 143.09, 139.05, 128.44, 114.16, 66.97, 62.02, 56.82, 40.62, 35.99, 33.88, 32.24, 29.44×2, 29.18×2, 28.98, 29.26, 23.33.

EXAMLE 8

(S)-1-(6-Cyclobutyl-hexyl)-3-(1-methyl-pyrrolidin-2-yl)pyridinium bromide hydrobromide salt (NCyNB-4)

8a. 6-Oxo-hexanoic acid methyl ester

A solution of ε-caprolactone (11.4 g, 0.100 mol), MeOH (300 mL) and concentrated H$_2$SO$_4$ (5 mL) was refluxed overnight. The resulting mixture was cooled to room temperature and concentrated. Water was added to the residue and the pH was adjusted to 7 with solid NaHCO$_3$. The aqueous layer was extracted with ether. The combined organic layers were washed with water, dried and concentrated to give 6-hydroxy-hexanoic acid methyl ester as a colorless oil, which was used in the next step without further purification.

The foregoing crude product was dissolved in CH$_2$Cl$_2$ (300 mL). Sodium acetate (2.6 g, 32 mmol) and PCC (32.7 g, 50 mmol) was added. After being stirred at room temperature for 2 h, ether (2000 mL) was added, the reaction mixture was filtered through Florisil, and the filtrate was concentrated. The residue was distilled at reduced pressure (80–84° C. at 0.2 mmHg) to give 6-oxo-hexanoic acid methyl ester (8.58 g, 60%) as a colorless oil: $^1$H NMR (300 MHz, CDCl$_3$) δ 9.72 (1H, t, J=1.5 Hz), 3.62 (3H, s), 2.43 (2H, m), 2.29 (2H, m), 1.62 (4H, m); $^{13}$C NMR (75 MHz, CDCl$_3$) δ 201.99, 173.64, 51.73, 43.66, 33.88, 24.53, 21.69.

8b. 6-Cyclobutylidene-hexanoic acid methyl ester

To a stirred suspension of KOtBu (4.81 g, 42.8 mmol) in tert-butyl methyl ether (tBuOMe) (50 mL) was added (4-bromobutyl)triphenylphosphonium bromide (10.45 g, 21.9 mmol). The resulting mixture was refluxed for 15 min and allowed to cool to room temperature. A solution of 6-oxo-hexanoic acid methyl ester (3.14 g, 21.8 mmol) in tBuOMe (5 mL) was added quickly and the resulting mixture was stirred overnight. Water (30 mL) was added. The aqueous phase was extracted with hexane. The combined organic phases were washed with saturated aqueous NH$_4$Cl and brine and dried. Concentration and purification of the residue by flash chromatography on silica gel (hexane:ethyl acetate, 10:1) afforded 6-cyclobutylidene-hexanoic acid methyl ester (1.27 g, 32%) as a colorless oil: $^1$H NMR (300 MHz, CDCl$_3$) δ 5.00 (1H, m), 3.64 (3H, s), 2.60 (4H, m), 2.28 (2H, t, J=7.8 Hz), 1.88 (4H, m), 1.60 (2H, m), 1.32 (2H, m); $^{13}$C NMR (75 MHz, CDCl$_3$) δ 174.25, 140.29, 119.88, 51.66, 34.23, 31.09, 29.47, 29.44, 27.75, 24.76, 17.28.

8c. 6-Cyclobutyl-hexan-1-ol

To a stirred solution of 6-cyclobutylidene-hexanoic acid methyl ester (0.60 g, 3.3 mmol) in toluene (30 mL) was added DIBAL-H (8.2 mL, 1 M solution in hexane, 8.2 mmol) dropwise at 0° C. under N$_2$. After stirring at 0° C. for 30 min, the reaction was quenched by MeOH (3 mL). Saturated aqueous sodium potassium tartrate (20 mL) was added to the reaction mixture. After stirrng for 1 h, the organic layer was separated and the aqueous phase was extracted with ether. The combined organic layers were washed with water and brine and dried. Evaporation of the solvent gave 6-cyclobutylidene-hexan-1-ol as a colorless oil, which was used in the next step without further purification.

A solution of the foregoing product in MeOH (20 mL) was hydrogenated with Pd—C (0.12 g, 10% w/w) in a Parr apparatus at 50 psi of H$_2$ overnight. The catalyst was removed by filtration, and the filtrate was evaporated under reduced pressure to give 6-cyclobutyl-hexan-1-ol (0.48 g, 88%) as a colorless oil: $^1$H NMR (300 MHz, CDCl$_3$) δ 3.62 (2H, t, J=6.6 Hz), 2.22 (1H, m), 2.03 (2H, m), 1.80 (2H, m), 1.55 (5H, m), 1.10–1.40 (8H, m); $^{13}$C NMR (75 MHz, CDCl$_3$) δ 63.28, 37.25, 36.42, 33.05, 29.71, 28.68, 27.40, 26.04, 18.78.

8d. (6-Bromo-hexyl)-cyclobutane

To a solution of 6-cyclobutyl-hexan-1-ol (0.47 g, 3.0 mmol) in DMF (10 mL) was added triphenylphosphine (0.88 g, 3.4 mmol). The solution was cooled to 0° C. and NBS (0.57 g, 3.2 mmol) was added in portions. After stirring for 30 min at room temperature, the reaction was quenched with methanol (0.5 mL). The solution was diluted with ether (60 mL), washed with water, saturated aqueous NaHCO$_3$ and brine successively. The organic layer was dried and concentrated. The residue was purified by flash chromatography on silica gel, eluting with hexane to afford (6-bromo-hexyl)-cyclobutane (0.60 g, 91%) as a colorless oil: $^1$H NMR (300 MHz, CDCl$_3$) δ 3.40 (2H, t, J=6.9 Hz), 2.23 (1H, m), 2.02 (2H, m), 1.82 (4H, m), 1.55 (2H, m), 1.12–1.46 (8H, m); $^{13}$C NMR (75 MHz, CDCl$_3$) δ 37.19, 36.39, 34.40, 33.11, 29.07, 28.68, 28.51, 27.26, 18.80.

8e. (S)-1-(6-Cyclobutyl-hexyl)-3-(1-methyl-pyrrolidin-2-yl)-pyridinium bromide hydrobromide salt (NCyNB-4)

To a stired solution of (S)-nicotine (0.18 g, 1.1 mmol) in AcOH (4 ml) was added (6-bromo-hexyl)cyclobutane (0.59 g, 2.7 mmol). The mixture was heated at reflux for 3 days. AcOH was evaporated and the residue was recrystallized in ethyl acetate-CHCl$_3$ to afford (S)-1-(6-cyclobutyl-hexyl)-3-(1-methyl-pyrrolidin-2-yl)-pyridinium bromide hydrobromide salt (NCyNB4) (0.31 g, 61%) as hygroscopic white crystals: $^1$H NMR (300 MHz, CDCl$_3$) δ 11.64 (1H, s), 10.42 (1H, s), 9.54 (1H, d, J=8.1 Hz), 9.06 (1H, d, J=6.0 Hz), 8.27 (1H, dd, J=8.1, 6.0 Hz), 5.74 (1H, m), 4.78 (2H, m), 3.98 (1H, m), 3.34 (1H, m), 2.96 (3H, d, J=5.1 Hz), 2.73 (1H, m), 2.44 (3H, m), 2.14 (3H, m), 1.96 (2H, m), 1.75 (2H, m), 1.51 (2H, m), 1.33 (6H, m), 1.16 (2H, m); $^{13}$C NMR (75 MHz, CDCl$_3$) δ 147.61, 146.61, 144.67, 134.77, 128.91, 67.09, 63.07, 56.09, 38.71, 36.99, 36.17, 32.06, 31.76, 29.20, 28.60, 27.14, 26.53, 21.89, 18.72; Anal. Calcd for C$_{20}$H$_{34}$Br$_2$N$_2$.0.1H$_2$O: C, 51.56; H, 7.44; N, 6.01. Found: C, 51.70; H, 7.45; N, 5.96.

EXAMPLE 9

(S)-1-(6-Cyclopentyl-hexyl)-3-(1-methyl-pyrrolidin-2-yl)-pyridinium bromide hydrobromide salt (NCyNB-5)

9a. 6-Cyclopentylidene-hexanoic acid methyl ester

To a stirred suspension of cyclopentyltriphenylphosphonium bromide (10.0 g, 23.8 mmol) in TMF (60 mL) was added dropwise n-BuLi (10.2 mL, 2.5 M solution in hexanes, 23.8 mmol) at 0° C. under N$_2$. The resulting solution was stirred at this temperature for 30 min and cooled to −78° C. A solution of 6-oxo-hexanoic acid methyl ester (3.33 g, 23.1 mmol) in THF (6 mL) was added quickly. The resulting mixture was then allowed to warm to room temperature and stirred overnight. Water (30 mL) was added. The aqueous phase was extracted with hexane. The combined organic phases were washed with saturated aqueous $NH_4Cl$ and brine and dried. Concentration and purification of the residue by flash chromatography on silica gel (hexane:ethyl acetate, 10:1) afforded 6-cyclopentylidene-hexanoic acid methyl ester (3.15 g, 70%) as a colorless oil: $^1H$ NMR (300 MHz, $CDCl_3$) δ 5.20 (1H, m), 3.64 (3H, s), 2.29 (2H, m), 2.16 (4H, m), 1.96 (2H, m), 1.62 (6H, m), 1.35 (2H, m); $^{13}C$ NMR (75 MHz, $CDCl_3$) δ 174.26, 143.54, 119.65, 51.66, 34.29, 33.79, 29.44, 28.86, 26.69, 26.61, 24.91.

9b. 6-Cyclopentylidene-hexan-1-ol

To a stirred solution of 6-cyclopentylidene-hexanoic acid methyl ester (2.77 g, 14.1 mmol) in toluene (130 mL) was added DIBAL-H (35.3 mL, 1 M solution in hexane, 35.3 mmol) dropwise at 0° C. under $N_2$. After sting at 0° C. for 30 min, the reaction was quenched by MeOH (10 mL). Saturated aqueous sodium potassium tartrate (80 mL) was added to the reaction mixture. After stirring for 1 h, the organic layer was separated and the aqueous phase was extracted with ether. The combined organic layers were washed with water and brine and dried. Evaporation of the solvent gave 6-cyclopentylidene-hexan-1-ol (2.47 g, 98%) as a colorless oil: $^1H$ NMR (300 MHz, $CDCl_3$) δ 5.24 (1H, m), 3.63 (2H, t, J=6.6 Hz), 2.21 (4H, m), 1.97 (2H, m), 1.50–1.70 (6H, m), 1.34 (2H, m); $^{13}C$ NMR (75 MHz, $CDCl_3$) δ 143.28, 120.08, 63.22, 33.82, 33.00, 29.81, 29.75, 28.87, 26.72, 26.63, 25.73.

9c. 6-Cyclopentyl-hexan-1-ol

A solution of 6-cyclopentylidene-hexan-1-ol (1.15 g, 6.85 mmol) in MeOH (50 mL) was hydrogenated with Pd—C (0.25 g, 10% w/w) in a Parr apparatus at 50 psi of $H_2$ overnight. The catalyst was removed by filtration, and the filtrate was evaporated under reduced pressure to give 6-cyclopentyl-hexan-1-ol (1.30 g, 100%) as a colorless oil: $^1H$ NMR (300 MHz, $CDCl_3$) δ 3.63 (2H, t, J=6.6 Hz), 1.42–1.64 (6H, m), 1.20–1.40 (8H, m), 1.04(2H, m); $^{13}C$ NMR (75 MHz, $CDCl_3$) δ 63.28, 40.41, 36.43, 33.06, 33.00, 29.98, 29.04, 26.05, 25.47.

9d. (6-Bromo-hexyl)-cyclopentane

To a solution of 6-cyclopentyl-hexan-1-ol (1.20 g, 7.06 mmol) in DMF (20 mL) was added triphenylphosphine (2.08 g, 7.93 mmol). The solution was cooled to 0° C. and NBS (1.36 g, 7.64 mmol) was added in portions. After stirring for 30 min at room temperature, the reaction was quenched with methanol (1 mL). The solution was diluted with ether (100 mL), washed with water, saturated aqueous $NaHCO_3$ and brine successively. The organic layer was dried and concentrated. The residue was purified by flash chromatography on silica gel, eluting with hexane to afford (6-bromo-hexyl)-cyclopentane (1.55 g, 94%) as a colorless oil: $^1H$ NMR (300 MHz, $CDCl_3$) δ 3.40 (2H, t, J=6.9 Hz), 1.85 (2H, m), 1.73 (3H, m), 1.38–1.64 (6H, m), 1.24–1.38 (6H, m), 1.04 (2H, m); $^{13}C$ NMR (75 MHz, $CDCl_3$) δ 40.38, 36.37, 34.35, 33.12, 32.99, 29.33, 28.87, 28.49, 25.46.

9e. (S)-1-(6-Cyclopentyl-hexyl)-3-(1-methyl-pyrrolidin-2-yl)-pyridinium bromide hydrobromide salt (NCyNB-5)

To a stirred solution of (S)-nicotine (0.43 g, 2.6 mmol) in AcOH (10 ml) was added (6-bromo-hexyl)-cyclopentane (1.50 g, 6.44 mmol). The mixture was heated at reflux for 3 days. AcOH was evaporated and the residue was recrystallized in ethyl acetate-$CHCl_3$ to afford (S)-1-(6-cyclopentyl-hexyl)-3-(1-methyl-pyrrolidin-2-yl)-pyridinium bromide hydrobromide salt (NCyNB-5) (0.68 g, 54%) as hygroscopic white crystals: $^1H$ NMR (300 MHz, $CDCl_3$) δ 11.74 (1H, s), 10.52 (1H, s), 9.62 (1H, d, J=8.4 Hz), 8.99 (1H, d, J=6.0 Hz), 8.29 (1H, dd, J=7.8, 6.3 Hz), 5.80 (1H, m), 4.78 (2H, m), 4.01 (1H, m), 3.35 (1H, m), 2.98 (3H, d, J=5.1 Hz), 2.76 (1H, m), 2.45 (3H, m), 2.15 (2H, m), 1.70 (3H, m), 1.15–1.60 (12H, m), 1.02 (2H, m); $^{13}C$ NMR (75 MHz, $CDCl_3$) δ 147.78, 146.78, 144.41, 134.94, 128.90, 67.03, 63.14, 56.10, 40.26, 38.72, 36.23, 32.96, 32.11, 31.82, 29.48, 28.77, 26.55, 25.43, 21.89; Anal. Calcd for $C_{21}H_{36}Br_2N_2 \cdot 0.2H_2O$: C, 52.55; H, 7.64; N, 5.84. Found: C, 52.41; H, 7.56; N, 5.78.

EXAMPLE 10

(S)-1-(6-Cyclohexyl-hexyl)-3-(1-methyl-pyrrolidin-2-yl)-pyridinium bromide hydrobromide salt (NCyNB-6)

10a. 6-Cyclohexylidene-hexanoic acid methyl ester

To a stirred suspension of cyclohexyltriphenylphosphonium bromide (8.40 g, 19.8 mmol) in THF (50 mL) was added dropwise n-BuLi (8.70 mL, 2.5 M solution in hexanes, 21.8 mmol) at 0° C. under $N_2$. The resulting solution was stirred at this temperature for 30 min and cooled to −78° C. A solution of 6-oxo-hexanoic acid methyl ester (2.84 g, 19.7 mmol) in THF (6 mL) was added quickly. The resulting mixture was then allowed to warm to room temperature and stirred overnight. Water (30 mL) was added. The aqueous phase was extracted with hexane. The combined organic phases were washed with saturated aqueous $NH_4Cl$ and brine and dried. Concentration and purification of the residue by flash chromatography on silica gel (hexane:ethyl acetate, 10:1) afforded 6-cyclohexylidene-hexanoic acid methyl ester (2.02 g, 49%) as a colorless oil: $^1H$ NMR (300 MHz, $CDCl_3$) δ 5.03 (1H, t, J=6.6 Hz), 3.64 (3H, s), 2.29 (2H, m), 2.03 (6H, m), 1.61 (2H, m), 1.41–1.54 (6H, m), 1.34 (2H, m); $^{13}C$ NMR (75 MHz, $CDCl_3$) δ 174.26, 140.05, 120.82, 51.66, 37.40, 34.26, 29.89, 28.93, 28.08, 27.20, 26.89, 24.79.

10b. 6-Cyclohexylidene-hexan-1-ol

To a stired solution of 6-cyclohexylidene-hexanoic acid methyl ester (1.28 g, 6.10 mmol) in toluene (60 mL) was added DIBAL-H (15.3 mL, 1 M solution in hexane, 15.3 mmol) dropwise at 0° C. under $N_2$. After stirring at 0° C. for 30 min, the reaction was quenched by MeOH (5 mL). Saturated aqueous sodium potassium tartrate (40 mL) was added to the reaction mixture. After string for 1 h, the organic layer was separated and the aqueous phase was extracted with ether. The combined organic layers were washed with water and brine and dried. Evaporation of the solvent gave 6-cyclohexylidene-hexan-1-ol (1.12 g, 100%) as a colorless oil: $^1H$ NMR (300 MHz, $CDCl_3$) δ 5.05 (1H, m), 3.62 (2H, t, J=6.6 Hz), 2.05 (6H, m), 1.42–1.64 (8H, m), 1.34 (2H, m); $^{13}C$ NMR (75 MHz, $CDCl_3$) δ 139.78, 121.25, 63.22, 37.43, 32.96, 30.22, 28.96, 28.11, 27.23, 25.58.

10c. 6-Cyclohexyl-hexan-1-ol

A solution of 6-cyclohexylidene-hexan-1-ol (1.05 g, 5.77 mmol) in MEOH (40 mL) was hydrogenated with Pd—C (0.23 g, 10% w/w) in a Parr apparatus at 50 psi of $H_2$ overnight. The catalyst was removed by filtration, and the filtrate was evaporated under reduced pressure to give 6-cyclohexyl-hexan-1-ol (1.02 g, 96%) as a colorless oil: $^1H$ NMR (300 MHz, $CDCl_3$) δ 3.63 (2H, t, J=6.6 Hz), 1.46–1.80 (7H, m), 1.04–1.44 (12H, m), 0.86 (2H, m); $^{13}C$ NMR (75 MHz, $CDCl_3$) δ 63.33, 37.92, 37.74, 33.72, 33.08, 30.04, 27.10, 27.04, 26.73, 26.05.

10d. (6-Bromo-hexyl)-cyclohexane

To a solution of 6-cyclohexyl-hexan-1-ol (0.98 g, 5.3 mmol) in DMF (15 mL) was added triphenylphosphine (1.56 g, 5.9 mmol). The solution was cooled to 0° C. and NBS (1.02 g, 5.7 mmol) was added in portions. After stirring for 30 min at room temperature, the reaction was quenched with methanol (0.6 mL). The solution was diluted with ether (80 mL), washed with water, saturated aqueous $NaHCO_3$ and brine successively. The organic layer was dried and concentrated. The residue was purified by flash chromatography on silica gel, eluting with hexane to afford (6-bromo-hexyl)-cyclohexane (1.16 g, 89%) as a colorless oil: $^1$H NMR (300 MHz, $CDCl_3$) δ 3.41 (2H, t, J=7.2 Hz), 1.85 (2H, m), 1.66 (5H, m), 1.42 (2H, m), 1.08–1.36 (10H, m), 0.88 (2H, m); $^{13}$C NMR (75 MHz, $CDCl_3$) δ 37.91, 37.68, 34.37, 33.72, 33.14, 29.39, 28.51, 27.04, 26.96, 26.73.

10e. (S)-1-(6-Cyclohexyl-hexyl)-3-(1-methyl-pyrrolidin-2-yl)-pyridinium bromide hydrobromide salt (NCyNB-6)

To a stirred solution of (S)-nicotine (0.31 g, 1.9 mmol) in AcOH (8 ml) was added (6-bromo-hexyl)-cyclohexane (1.15 g, 4.65 mmol). The mixture was heated at reflux for 3 days. AcOH was evaporated and the residue was recrystallized in ethyl acetate-$CHCl_3$ to afford (S)-1-(6-cyclohexyl-hexyl)-3-(1-methyl-pyrrolidin-2-yl)-pyridinium bromide hydrobromide salt (NCyNB-6) (0.59 g, 63%) as hygroscopic white crystals: $^1$H NMR (300 MHz, $CDCl_3$) δ 11.71 (1H, s), 10.44 (1H, s), 9.58 (1H, d, J=8.1 Hz), 9.04 (1H, d, J=6.0 Hz), 8.29 (1H, dd, J=7.8, 6.0 Hz), 5.75 (1H, m), 4.78 (2H, m), 4.02 (1H, m), 3.37 (1H, m), 2.98 (3H, d, J=4.8 Hz), 2.75 (1H, m), 2.48 (3H, m), 2.13 (2H, m), 1.65 (5H, m), 1.05–1.45 (12H, m), 0.83 (2H, m); $^{13}$C NMR (75 MHz, $CDCl_3$) δ 147.66, 146.65, 144.57, 134.85, 128.93, 67.09, 63.11, 56.09, 38.71, 37.77, 37.52, 33.61, 32.09, 31.80, 29.53, 26.92, 26.84, 26.63, 26.54, 21.89; Anal. Calcd for $C_{22}H_{38}Br_2N_2 \cdot 0.3H_2O$: C, 53.30; H, 7.85; N, 5.65. Found: C, 53.35; H, 7.74; N, 5.70.

EXAMPLE 11

(S)-3-(1-Methyl-pyrrolidin-2-yl)-1-oct-3-ynyl-pyridinium bromide (NONB-3y)

11a. 1-Bromo-oct-3-yne

To a solution of oct-3-yn-1-ol (1.26 g, 10.0 mmol) in DMF (25 mL) was added triphenylphosphine (2.92 g, 11.2 mmol). The solution was cooled to 0° C. and NBS (1.92 g, 10.8 mmol) was added in portions. After stirring for 30 min at room temperature, the reaction was quenched with methanol (1 mL). The solution was diluted with ether (150 mL), washed with water, saturated aqueous $NaHCO_3$ and brine successively. The organic layer was dried and concentrated. The residue was purified by flash chromatography on silica gel, eluting with hexane to afford 1-bromo-oct-3-yne (1.35 g, 71%) as a colorless oil: $^1$H NMR (300 MHz, $CDCl_3$) δ 3.40 (2H, d, J=7.2 Hz), 2.78 (2H, m), 2.15 (2H, m), 1.22 (4H, m), 0.88 (3H, t, J=6.9 Hz); $^{13}$C NMR (75 MHz, $CDCl_3$) δ 82.83, 77.05, 31.18, 30.63, 23.68, 22.20, 18.67, 13.89.

11b. (S)-3-(1-Methyl-pyrrolidin-2-yl)-1-oct-3-ynyl-pyridinium bromide (NONB-3y)

To a stirred solution of (S)-nicotine (0.41 g, 2.5 mmol) in AcOH (10 ml) was added 1-bromo-oct-3-yne (1.16 g, 6.14 mmol). The mixture was heated at reflux for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 0.50 g (56%) of (S)-3-(1-methyl-pyrrolidin-2-yl)-1-oct-3-ynyl-pyridinium bromide (NONB-3y) as a brown oil. $^1$H NMR (300 MHz, $CDCl_3$) δ 9.74 (1H, d, J=5.1 Hz), 9.15 (1H, s), 8.43 (1H, d, J=7.8 Hz), 8.04 (1H, dd, J=7.8, 5.1 Hz), 5.13 (2H, m), 3.51 (1H, t, J=7.8 Hz), 3.23 (1H, m), 3.00 (2H, m), 2.42 (2H, m), 2.22 (3H, s), 2.01 (2H, m), 1.89 (2H, m), 1.64 (2H, m), 1.28 (4H, m), 0.82 (3H, t, J=7.2 Hz); $^{13}$C NMR (75 MHz, $CDCl_3$) δ 145.97, 144.38, 144.10, 143.57, 128.00, 86.12, 74.07, 67.30, 60.72, 56.92, 40.74, 36.11, 30.94, 23.14, 22.50, 22.16, 18.54, 13.80; Anal. Calcd for $C_{18}H_{27}BrN_2 \cdot 0.5H_2O$: C, 60.00; H, 7.83; N, 7.77. Found: C, 60.15; H, 7.92; N, 6.92.

EXAMPLE 12

(S)-1-Dec-3-ynyl-3-(1-methyl-pyrrolidin-2-yl)-pyridinium bromide (NDNB-3y)

12a. 1-bromo-dec-3-yne

To a solution of dec-3-yn-1-ol (1.54 g, 10.0 mmol) in DMF (25 mL) was added triphenylphosphine (2.92 g, 11.2 mmol). The solution was cooled to 0° C. and NBS (1.92 g, 10.8 mmol) was added in portions. After stirring for 30 min at room temperature, the reaction was quenched with methanol (1 mL). The solution was diluted with ether (150 mL), washed with water, saturated aqueous $NaHCO_3$ and brine successively. The organic layer was dried and concentrated. The residue was purified by flash chromatography on silica gel, eluting with hexane to afford 1-bromo-dec-3-yne (1.57 g, 72%) as a colorless oil: $^1$H NMR (300 MHz, $CDCl_3$) δ 3.40 (2H, d, J=7.2 Hz), 2.70 (2H, m), 2.14 (2H, m), 1.20–1.55 (8H, m), 0.88 (3H, t, J=6.9 Hz); $^{13}$C NMR (75 MHz, $CDCl_3$) δ 82.89, 77.05, 31.62, 30.68, 29.06, 28.78, 23.65, 22.86, 18.99, 13.38.

12b. (S)-1-Dec-3-ynyl-3-(1-methyl-pyrrolidin-2-yl)-pyridinium bromide (NDNB-3y)

To a stirred solution of (S)-nicotine (0.46 g, 2.8 mmol) in AcOH (15 ml) was added 1-bromo-dec-3-yne (1.50 g, 6.91 mmol). The mixture was heated at reflux for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 0.55 g (51%) of (S)-1-dec-3-ynyl-3-(1-methyl-pyrrolidin-2-yl)-pyridinium bromide (NDNB-3y) as a brown oil. $^1$H NMR (300 MHz, $CDCl_3$) δ 9.77 (1H, d, J=5.7 Hz), 9.14 (1H, s), 8.43 (1H, d, J=8.1 Hz), 8.04 (1H, dd, J=8.1, 5.7 Hz), 5.16 (2H, m), 3.52 (1H, t, J=8.1 Hz), 3.27 (1H, m), 3.03 (2H, m), 2.47 (2H, m), 2.26 (3H, s), 1.85–2.10 (4H, m), 1.70 (1H, m), 1.15–1.45 (8H, m), 0.86 (3H, t, J=7.2 Hz); $^{13}$C NMR (75 MHz, $CDCl_3$) δ 145.91, 144.24, 144.12, 143.57, 128.02, 86.16, 73.98, 67.24, 60.66, 56.87, 40.70, 36.05, 31.44, 28.86, 28.75, 23.36, 22.71, 22.45, 18.82, 14.27; Anal. Calcd for $C_{20}H_{31}BrN_2 \cdot 0.7H_2O$: C, 61.28; H, 8.33; N, 7.15. Found: C, 61.14; H, 8.21; N, 7.14.

EXAMPLE 13

(S)-1-(7-Methyl-oct-6-enyl)-3-(1-methyl-pyrrolidin-2-yl)-pyridinium bromide hydrobromide (NONB-6e7M)

13a. 7-Methyl-oct-6-enoic acid methyl ester

To a stirred suspension of isopropyltriphenylphosphonium bromide (10.9 g, 28.3 mmol) in THF (60 mL) was added dropwise n-BuLi (12.0 mL, 2.5 M solution in hexanes, 30.0 mmol) at 0° C. under $N_2$. The resulting solution was stirred at this temperature for 30 min and cooled to −78° C. A solution of 6-oxo-hexanoic acid methyl ester (3.95 g, 19.7 mmol) in THF (10 mL) was added quickly. The resulting mixture was then allowed to warm to room temperature and stirred overnight. Water (30 mL) was added. The aqueous phase was extracted with hexane. The combined organic phases were washed with saturated aqueous NH$_4$Cl and brine and dried. Concentration and purification of the residue by flash chromatography on silicagel (hexane: ethyl acetate, 10:1) afforded 7-methyl-oct-6-enoic acid methyl ester (3.39 g, 72%) as a colorless oil: $^1$H NMR (300 MHz, CDCl$_3$) δ 5.08 (1H, m), 3.64 (3H, s), 2.29 (2H, t, J=7.2 Hz), 1.97 (2H, m), 1.66 (3H, s), 1.62 (2H, m), 1.58 (3H, s), 1.36 (2H, m); $^{13}$C NMR (75 MHz, CDCl$_3$) δ 174.26, 140.05, 131.80, 124.27, 51.67, 34.29, 29.60, 27.89, 25.97, 24.87, 17.94.

13b. 7-Methyl-oct-6-en-1-ol

To a stirred solution of 7-methyl-oct-6-enoic acid methyl ester (3.29 g, 19.4 mmol) in toluene (180 mL) was added DIBAL-H (48.5 mL, 1 M solution in hexane, 48.5 mmol) dropwise at 0° C. under N$_2$. After stirring at 0° C. for 30 min, the reaction was quenched by MeOH (12 mL). Saturated aqueous sodium potassium tartrate (120 mL) was added to the reaction mixture. After stirring for 1 h, the organic layer was separated and the aqueous phase was extracted with ether. The combined organic layers were washed with water and brine and dried. Evaporation of the solvent gave 7-methyl-oct-6-en-1-ol (2.70 g, 98%) as a colorless oil: $^1$H NMR (300 MHz, CDCl$_3$) δ 5.11 (1H, m), 3.63 (2H, m), 1.99 (2H, m), 1.68 (3H, s), 1.59 (3H, s), 1.53 (2H, m), 1.25–1.45 (4H, m); $^{13}$C NMR (75 MHz, CDCl$_3$) δ 131.52, 124.69, 63.25, 33.00, 29.95, 28.25, 26.02, 25.69, 17.98.

13c. 8-Bromo-2-methyl-oct-2-ene

To a solution of 7-methyl-oct-6-en-1-ol (1.00 g, 7.04 mmol) in DMF (18 mL) was added triphenylphosphine (2.06 g, 7.85 mmol). The solution was cooled to 0° C. and NBS (1.35 g, 7.58 mmol) was added in portions. After stirring for 30 min at room temperature, the reaction was quenched with methanol (1 mL). The solution was diluted with ether (100 mL), washed with water, saturated aqueous NaHCO$_3$ and brine successively. The organic layer was dried and concentrated. The residue was purified by flash chromatography on silica gel, eluting with hexane to afford 8-bromo-2-methyl-oct-2-ene (1.11 g, 77%) as a colorless oil: $^1$H NMR (300 MHz, CDCl$_3$) δ 5.10 (1H, m), 3.40 (2H, t, J=6.9 Hz), 1.98 (2H, m), 1.86 (2H, m), 1.68 (3H, d, J=0.9 Hz), 1.60 (3H, d, J=0.3 Hz), 1.42 (2H, m), 1.41 (4H, m); $^{13}$C NMR (75 MHz, CDCl$_3$) δ 132.08, 124.81, 34.59, 33.44, 29.64, 28.49, 28.44, 26.36, 18.35.

13d. (S)-1-(7-Methyl-oct-6-enyl)-3-(1-methyl-pyrrolidin-2-yl)-pyridinium bromide hydrobromide (NONB-6e7M)

To a stired solution of (S)-nicotine (0.33 g, 2.0 mmol) in AcOH (10 ml) was added 8-bromo-2-methyl-oct-2-ene (1.05 g, 5.12 mmol). The mixture was heated at reflux for 3 days. AcOH was evaporated and the residue was recrystallized in ethyl acetate-CHCl$_3$ to (S)-1-(7-methyl-oct-6-enyl)-3-(1-methyl-pyrrolidin-2-yl)-pyridinium bromide hydrobromide (NONB-6e7M) (0.58 g, 63%) as hygroscopic white crystals: $^1$H NMR (300 MHz, CDCl$_3$) δ 11.61 (1H, s), 10.38 (1H, s), 9.52 (1H, d, J=8.1 Hz), 9.17 (1H, d, J=6.0 Hz), 8.31 (1H, dd, J=8.1, 6.0 Hz), 5.75 (1H, m), 5.03(1H, m), 4.81 (2H, m), 4.00 (1H, m), 3.37 (1H, m), 2.98 (3H, s), 1.80–2.25 (4H, m), 1.64 (3H, s), 1.55 (3H, s), 1.39 (4H, m); $^{13}$C NMR (75 MHz, CDCl$_3$) δ 147.49, 146.49, 144.86, 134.65, 132.20, 128.91, 123.74, 67.14, 62.95, 56.09, 38.69, 32.02, 31.67, 29.34, 27.87, 26.04, 21.91, 18.05; Anal. Calcd for C$_{19}$H$_{32}$Br$_2$N$_2$.0.7H$_2$O: C, 49.52; H, 7.28; N, 6.08. Found: C, 49.44; H, 7.18; N, 6.07.

EXAMPLE 14

(S)-1-(7-Methyl-octyl)-3-(1-methyl-pyrrolidin-2-yl)-pyridinium bromide hydrobromide salt (NONB-7M)

14a. 7-Methyl-octan-1-ol

A solution of 7-methyl-oct-6-en-1-ol (1.42 g, 10.0 mmol) in MeOH (70 mL) was hydrogenated with Pd—C (0.40 g, 10% w/w) in a Parr apparatus at 50 psi of H$_2$ overnight. The catalyst was removed by filtration, and the filtrate was evaporated under reduced pressure to give 7-methyl-octan-1-ol (1.38 g, 96%) as a colorless oil: $^1$H NMR (300 MHz, CDCl$_3$) δ 3.64 (2H, t, J=6.6 Hz), 1.54 (3H, m), 1.10–1.44 (8H, m), 0.88 (3H, s), 0.85 (3H, s); $^{13}$C NMR (75 MHz, CDCl$_3$) δ 63.28, 39.21, 33.06, 29.98, 28.24, 27.64, 26.06, 22.94.

14b. 1-Bromo-7-methyl-octane

To a solution of 7-methyl-octan-1-ol (1.20 g, 8.33 mmol) in DMF (20 mL) was added triphenylphosphine (2.43 g, 9.26 mmol). The solution was cooled to 0° C. and NBS (1.60 g, 8.99 mmol) was added in portions. After stirring for 30 min at room temperature, the reaction was quenched with methanol (1 mL). The solution was diluted with ether (100 mL), washed with water, saturated aqueous NaHCO$_3$ and brine successively. The organic layer was dried and concentrated. The residue was purified by flash chromatography on silica gel, eluting with hexane to afford 1-bromo-7-methyl-octane (1.28 g, 74%) as a colorless oil: $^1$H NMR (300 MHz, CDCl$_3$) δ 3.41 (2H, t, J=6.6 Hz), 1.85 (2H, m), 1.52 (1H, m), 1.42 (2H, m), 1.28 (4H, m), 1.17 (2H, m), 0.87 (3H, s), 0.85 (3H, s); $^{13}$C NMR (75 MHz, CDCl$_3$) δ 39.16, 34.34, 33.14, 29.34, 28.52, 28.24, 27.51, 22.94.

14c. (S)-1-(7-Methyl-octyl)-3-(1-methyl-pyrrolidin-2-yl)-pyridinium bromide hydrobromide salt (NONB-7M)

To a stirred solution of (S)-nicotine (0.37 g, 2.3 mmol) in AcOH (10 ml) was added 1-bromo-7-methyl-octane (1.20 g, 5.80 mmol). The mixture was heated at reflux for 3 days. AcOH was evaporated and the residue was recrystallized in ethyl acetate-CHCl$_3$ to (S)-1-(7-methyl-octyl)-3-(1-methyl-pyrrolidin-2-yl)-pyridinium bromide hydrobromide salt (NONB-7M) (0.60 g, 58%) as hygroscopic white crystals: $^1$H NMR (300 MHz, CDCl$_3$) δ 11.85 (1H, s), 10.61 (1H, s), 9.68 (1H, d, J=8.4 Hz), 8.83 (1H, d, J=6.0 Hz), 8.24 (1H, dd, J=8.1, 6.3 Hz), 5.80 (1H, m), 4.75 (2H, m), 4.01 (1H, m), 3.32 (1H, m), 2.96 (3H, d, J=4.8 Hz), 2.74 (1H, m), 2.30–2.60 (3H, m), 2.11 (2H, m), 1.05–1.55 (9H, m), 0.82 (6H, d, J=6.6 Hz); $^{13}$C NMR (75 MHz, CDCl$_3$) δ 147.64, 146.61, 144.97, 134.71, 129.09, 67.21, 63.13, 56.16, 38.97, 32.15, 31.82, 29.48, 28.10, 27.36, 26.55, 22.86, 21.97; Anal. Calcd for C$_{19}$H$_{34}$Br$_2$N$_2$.0.3H$_2$O: C, 50.09; H, 7.63; N, 6.15. Found: C, 50.08; H, 7.64; N, 6.13.

EXAMPLE 15

(S)-1-[2-(2-Ethoxy-ethoxy)-ethyl]-3-(1-methyl-pyrrolidin-2-yl)-pyridinium bromide (NONB-3O6O)

To a stirred solution of (S)-nicotine (0.67 g, 4.1 mmol) in AcOH (20 ml) was added 1-bromo-2-(2-ethoxy-ethoxy)-ethane (1.97 g, 10.0 mmol). The mixture was heated at reflux for 3 days. AcOH was evaporated and the residue was dissolved in CHCl$_3$. The mixture was washed with saturated aqueous NaHCO$_3$, water and brine successively and dried. Evaporation of the solvent followed by titration with ether afforded 0.56 g (38%) of (S)-1-[2-(2-ethoxy-ethoxy)-ethyl]-3-(1-methyl-pyrrolidin-2-yl)-pyridinium bromide (NONB-3O6O) as a brown oil. $^1$H NMR (300 MHz, CDCl$_3$) δ 9.65 (1H, d, J=6.0 Hz), 9.26 (1H, s), 8.44 (1H, d, J=7.8 Hz), 7.99 (1H, dd, J=7.8, 6.0 Hz), 5.27 (2H, t, J=4.8 Hz), 4.06 (2H, t, J=4.8 Hz), 3.64 (2H, m), 3.41–3.60 (5H, m), 3.26 (1H, m), 2.43 (2H, m), 2.25 (3H, s), 1.91 (2H, m), 1.60 (1H, m), 1.16 (3H, t, J=6.9 Hz); $^{13}$C NMR (75 MHz, CDCl$_3$) δ 145.87, 144.40×2, 144.02, 127.85, 70.83, 69.72, 69.57, 67.17, 66.77, 61.41, 56.91, 40.67, 36.02, 23.41, 15.47; Anal. Calcd for C$_{16}$H$_{27}$BrN$_2$.0.5H$_2$O: C, 52.18; H, 7.66; N, 7.61. Found: C, 52.22; H, 7.68; N, 7.50.

EXAMLE 16

(S)-1-(9-Acetoxy-nonyl)-3-(1-methyl-pyrrolidin-2-yl)-pyridinium bromide (NANNB)

To a stirred solution of (S)-nicotine (2.0 ml, 12.2 mmol) in AcOH (25 ml) 1,9 dibromononane (1.28 g, 6.2 mmol) was added. The mixture was refluxed for 3 days. After evaporation of the AcOH, the resulting residue was basified using saturated aqueous NaHCO$_3$. The resulting aqueous solution was extracted three times with ethyl ether followed by extraction three times with chloroform. The chloroform layers were collected, dried over magnesium sulfate. Evaporation of the solvent afforded 2.97 g (40%) of (S)-1-(9-acetoxy-nonyl)-3-(1-methyl-pyrrolidin-2-yl)-pyridinium bromide (NANNB) as a brown oil. $^1$H NMR (300 MHz, CDCl$_3$) δ 9.60 (1H, d), 9.15 (1H, s), 8.47 (1H, d), 8.10 (1H, t), 5.01 (2H, t), 4.04 (2H, t), 3.61 (1H, t), 3.29 (1H, t), 2.47 (2H, m), 2.28 (3H, s), 1.54–2.10 (10H, m), 1.39–1.18 (17H, m).

EXAMLE 17

(S)-1-(11-Acetoxy-undecyl)-3-(1-methyl-pyrrolidin-2-yl)-pyridinium bromide (NAUNB)

To a stirred solution of (S)-nicotine (2.0 ml, 12.5 mmol) in AcOH (25 ml) 1,11 dibromoundecane (1.47 ml, 6.2 mmol) was added. The mixture was refluxed for 3 days. After evaporation of the AcOH, the resulting residue was basified using saturated aqueous NaHCO$_3$. The resulting aqueous solution was extracted three times with ethyl ether followed by extraction three times with chloroform. The chloroform layers were collected, dried over magnesium sulfate. Evaporation of the solvent afforded 2.80 g (36%) of (S)-1-(11-acetoxy-undecyl)-3-(1-methyl-pyrrolidin-2-yl)-pyridinium bromide (NAUNB) as a brown oil. $^1$H NMR (300 MHz, CDCl$_3$) δ 9.58 (1H, d), 9.13 (1H, s), 8.46 (1H, d), 8.08 (1H, t), 4.99 (2H, t), 4.02 (2H, t), 3.62 (1H, t), 3.28 (1H, t), 2.48 (2H, m), 2.28 (3H, s), 1.53–2.00 (10H, m), 1.41–1.17 (17H, m).

EXAMPLE 18

(S)-1-(12-Acetoxy-dodecyl)-3-(1-methyl-pyrrolidin-2-yl)-pyridinium bromide (NADDNB)

To a stirred-solution of (S)-nicotine (0.603 ml, 3.75 mmol) in AcOH (25 ml) 1,12 dibromododecane (0.56 g, 1.71 mmol) was added. The mixture was refluxed for 3 days. After evaporation of the AcOH, the resulting residue was basified using saturated aqueous NaHCO$_3$. The resulting aqueous solution was extracted three times with ethyl ether followed by extraction three times with chloroform. The chloroform layers were collected, dried over magnesium sulfate. Evaporation of the solvent afforded 0.64 g (26%) of (S)-1-(12-acetoxy-dodecyl)-3-(1-methyl-pyrrolidin-2-yl)-pyridinium bromide (NADDNB) as a brown oil. $^1$H NMR (300 MHz, CDCl$_3$) δ 9.58 (1H, d), 9.14 (1H, s), 8.46 (1H, d), 8.08 (1H, t), 5.00 (2H, t), 4.04 (2H, t), 3.62 (1H, t), 3.29 (1H, t), 2.48 (2H, m), 2.28 (3H, s), 1.55–2.1(10, m), 1.42–1.19 (17, m); $^{13}$C NMR (75 MHz, CDCl$_3$) δ 171.3, 144.2, 144.0, 143.0, 128.4×2, 67.2, 64.8, 62.4, 56.9, 40.7, 36.0, 32.3, 29.7×2, 29.6, 29.5, 29.4, 29.3, 28.8, 26.4, 26.1, 23.4, 21.3.

EXAMPLE 19

[$^3$H]-DA Release Assay

Rat striatal slices (500 μm thickness, 6–8 mg wet weight) were incubated for 30 minutes in Kreb's buffer (118 mM NaCl, 4.7 mMKCl, 1.2 mM MgCl$_2$, 1.0 mM NaH$_2$PO$_4$, 1.3 mM CaCl$_2$, 11.1 mM glucose, 25 mM NaHCO$_3$, 0.11 mM L-ascorbic acid, and 0.004 mM disodium EDTA; pH 7.4, and saturated with 95% O$_2$/5% CO$_2$) in a metabolic shaker at 34° C. Slices were rinsed with 15 ml of fresh buffer and incubated for an additional 30 minutes in fresh buffer containing 0.1 μM [$^3$H]-DA (6 slices/3 ml). Subsequently, slices were rinsed with 15 ml of fresh buffer and transferred to a glass superfusion chamber. Slices were superfused (1.0 ml/min) for 60 minutes with Kreb's buffer containing nomifensine (10 μM) and pargyline (10 μM) and maintained at 34° C., pH 7.4, with continual aeration (95% O$_2$/5% CO$_2$). Two five minute samples (5 ml each) were collected to determine basal outflow of [$^3$H]-DA. Chain-modified NONI and NDNI analogs were added to the superfusion buffer after the collection of the second sample and remained in the buffer until 12 consecutive five minute samples were collected. Subsequently, S-(−)-nicotine (10 μM) was added to the buffer and an additional 12 consecutive five minute samples were collected. At the end of the experiment, each slice was solubilized and the [$^3$H] content of the tissue determined.

Radioactivity in the superfusate and tissue samples was determined by liquid scintillation spectroscopy. Fractional release for each sample was calculated by dividing by the total tritium present in the tissue at the time of sample collection, and was expressed as a percentage of total tissue tritium. Basal [$^3$H]outflow was calculated from the average of the tritium collected in the two five minute samples just before addition of the chain-modified NONI and NDNI analog. The sum of the increase in collected tritium resulting from either exposure to the test-compound or exposure to nicotine in the absence and presence of the test compound equaled total [$^3$H]overflow. [$^3$H]Overflow was calculated by subtracting the [$^3$H]outflow during an equivalent period of prestimulation from the values in samples collected during and after drug exposure. Inasmuch as the radiolabelled compounds were not separated and identified, the tritium collected in superfusate is referred to as either [$^3$H]outflow or [$^3$H]overflow, rather than as [$^3$H]-DA. [$^3$H]Overflow primarily represents [$^3$H]-DA in the presence of nomifensine and pargyline in the superfusion buffer.

The chain-modified NONI and NDNI analogs were evaluated for their ability to evoke [3H] release from rat striatal slices at three concentrations (0.1, 1 and 10 μM). In addition, the classical competitive nicotinic antagonist DHBE was also examined in this assay for comparison. None of the compounds examined at concentrations below 10 μM had any significant [$^3$H]-DA releasing properties in this assay. Since striatal NIC-evoked [$^3$H]-DA release is thought to be mediated through a mechanism involving the putative α3β2* receptor subtype, these compounds do not possess significant agonist activity at this subtype.

The chain-modified NONI and NDNI analogs were also evaluated for their ability to inhibit NIC evoked [$^3$H]-DA release. In these experiments, striatal slices were superfused for 60 minutes with various concentrations of the analogs prior to NIC (10 μM) exposure. Antagonist activity was evaluated by comparing the NIC-evoked [$^3$H]overflow in the absence and presence of the analogs. The relative order of potency of these chain-modified NONI and NDNI analogs for inhibition of NIC-evoked [$^3$H]-DA release from rat striatal slices is provided in Table 1 by a comparison of their $IC_{50}$ values.

TABLE 1

$IC_{50}$s for Chain-modified NONI and NDNI Analogs in the S-(−)-NIC-evoked [$^3$H]-DA Release Assay

| Compound | $IC_{50}$ (μM) |
|---|---|
| NONI | 0.62 |
| NDNI | >100 |
| DHβE | 3.60 |
| NONB-3t | 3.47 |
| NDNB-4t | 0.33 |
| NONB-3c | 2.02 |
| NDNB-4c | 1.48 |
| NONB-7e | 2.61 |
| NDNB-9e | |
| NUNB-10e | |
| NCyNB-4 | |
| NCyNB-5 | |
| NCyNB-6 | |
| NONB-3y | 1.68 |
| NDNB-3y | 2.59 |
| NONB-6e7M | 1.99 |
| NONB-7M | >100 |
| NONB-3O6O | |
| NANNB | |
| NADNI | |
| NADDNB | |

EXAMPLE 20

[$^3$H]-NIC Binding Assay

Striata from two rats were dissected, pooled, and homogenized with a Tekmar polytron in 10 volumes of ice-cold modified Krebs-HEPES buffer (20 mM HEPES, 118 mM NaCl, 4.8 mM KCl, 2.5 mM $CaCl_2$, 1.2 mM $MgSO_4$, adjusted to pH 7.5). The homogenates were incubated at 37° C. for 5 minutes and centrifuged at 15,000 g for 20 minutes. The pellet was resuspended in 10 volumes of ice-cold MilliQ water, incubated for 5 minutes at 37° C., and centrifuged at 15,000 g for 20 mm. The second pellet was then resuspended in 10 volumes of fresh ice-cold 10% Krebs-HEPES buffer, incubated at 37° C., and centrifuged at 15,000 g for 20 minutes. The latter sequence of resuspension, incubation, and rentrifugation was repeated. The pellet was frozen under fresh 10% Krebs-HEPES buffer and stored at −40° C. until assayed. Upon assay, the pellet was resuspended in the Krebs-HEPES buffer, incubated at 37° C. for 5 minutes, and centrifuged at 15,000 g for 20 mm. The final pellet was resuspended in 3.6 ml ice-cold MilliQ water which provided for approximately 200 μg protein per 100 μl aliquot. Competition assays were performed in triplicate in a final volume of 200 μl Krebs-HEPES buffer containing 250 mmol Tris buffer (pH 7.5 at 4° C.). Reactions were initiated by addition of 100 μl of membrane suspension to 3 nM [$^3$H]-NIC (50 μl) and one of at least nine concentrations of chain-modified NONI and NDNI analog (50 μl). After a 90 min incubation at 4° C., reactions were terminated by dilution of the samples with 3 ml of ice-cold Krebs-HEPES buffer followed immediately by filtration through Whatman GF/B glass fiber filters (presoaked in 0.5% polyethyleneimine) using a Brandel Cell Harvester. Filters were rinsed three times with 3 ml of ice-cold Krebs-HEPES buffer, transferred to scintillation vials, and 5 ml scintillation cocktail (Research Products International Corp., Mt. Prospect, Ill.) added. Nonspecific binding determined in triplicate was defined as binding in the presence of 10 μM NIC. Binding parameters were determined using the weighted, least squares nonlinear regression analysis.

The chain-modified NONI and NDNI analogs were evaluated for their ability to displace [$^3$H]-NIC binding from rat striatal membranes. The results are summarized in Table 2. Furthermore, the displacement by the analogs was compared to that produced by DHβE (Ki=150 nM).

TABLE 2

Specific Binding of [$^3$H]-NIC to Rat Striatal Nicotinic Acetylcholine Receptors in the Presence of chain-modified NONI and NDNI analogs

| Compound | $K_i$ (μM)[a] |
|---|---|
| NONI | 20 |
| NDNI | 0.093 |
| DHβE | 0.15 |
| NONB-3t | 3.97 |
| NDNB-4t | 0.32 |
| NONB-3c | 0.086 |
| NDNB-4c | 7.79 |
| NONB-7e | 0.45 |
| NDNB-9e | |
| NUNB-10e | |
| NCyNB-4 | 7.20 |
| NCyNB-5 | 5.54 |
| NCyNB-6 | 4.56 |
| NONB-3y | 0.20 |
| NDNB-3y | 0.81 |
| NONB-6e7M | 0.45 |
| NONB-7M | 0.44 |
| NONB-3O6O | 1.20 |
| NANNB | |
| NADNI | |
| NADDNB | |

[a]Data are expressed as fmol/mg of protein of at least 3 independent experiments. Specific binding is calculated as the difference between the total binding of 3 nM [$^3$H]-NIC to the receptors alone and nonspecific binding in the presence of 10 μM nicotine.

EXAMPLE 21

[$^3$H]-MLA Binding Assay

Rat brain tissue (without cortex, striatum and cerebellum) was homogenized with a Tekmar Polytron (setting 40) in 20 volumes of ice-cold hypotonic buffer (2 mM HEPES, 14.4 mM NaCl, 0.15 mM KCl, 0.2 mM $CaCl_2$ and 0.1 mM $MgSO_4$, pH=7.5). The homogenate was incubated at 37° C. for 10 minutes and centrifuged at 25,000×g for 15 minutes at 40° C. The pellet was washed 3 times more by resuspension in the 20 volumes of the same buffer and centrifugation at the above parameters. The final pellet was stored at −20° C. under 4.6 ml of the incubation buffer and was suspended just before the incubation with radioligand.

The binding of [$^3$H]methyllycaconitine ([$^3$H]MLA), a probe for the $\alpha_7$ neuronal nicotinic acetylcholine receptor subtype, was determined using a modification of the method of Davies et al., "Characterisation of the binding of [³H] methyllycaconitine: a new radioligand for labelling α7-type neuronal nicotinic acetylcholine receptors", *Neuropharmacology*, 38, 679–690 (1999). [³H]-MLA (25.4 Ci/mmol) was purchased from Tocris Cookson Ltd., Bristol, U.K. Binding was performed in duplicate, in a final volume of 250 μL of the incubation medium, containing 20 mM HEPES, 144 mM NaCl, 1.5 mM KCl, 2 mM CaCl₂, 1 mM MgSO₄ and 0.05% BSA, pH=7.5. Reaction was initiated by the addition of 100 μl of membrane suspension to the samples containing a desired concentration of test compounds and 2.5 nM [³H]-MLA (final concentration) and incubated for 2 hours at room temperature. Total binding was measured in the absence of unlabelled ligand, and nonspecific binding was determined in the presence of 1 μM unlabelled MLA. The binding reaction was terminated by dilution of samples with 3 ml of ice-cold incubation buffer followed by immediate filtration through presoaked in 0.5% polyethylenimine glass fiber filters (S&S, grade #32) using a Brandel harvester system. Filters were rinsed three times with 3 ml of ice-cold buffer, transferred to scintillation vials and 4 ml of scintillation cocktail was added. Protein was measured using the Bradford dye-binding procedure with bovine serum albumin as the standard.

In order to determine if these compounds have affinity at the α7 receptor subtype, the chain-modified NONI and NDNI analogs were evaluated for their ability to displace [³H]-MLA binding from rat brain membranes, as a reflection of their interaction with the α7 receptor (Table 3). In addition, the classical α7 receptor antagonist α-bungarotoxin was also examined in this assay for comparison. α-Bungarotoxin afforded a $K_i$ value of 7.2 nM in the above assay. The results from the competition binding assay showed that NCyNB-4, NCyNB-5, and NCyNB-6 had Ki's of 30.3 μM, 88.7 μM, and 42.7 μM, respectively. None of the other chain-modified NONI and NDNI analogs possessed any significant binding affinity in the [3H]-MLA assay at concentration>100 μM.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

What is claimed is:

1. A compound including resolved enantiomers and diastereoisomers thereof selected from a formula consisting of formula (VI):

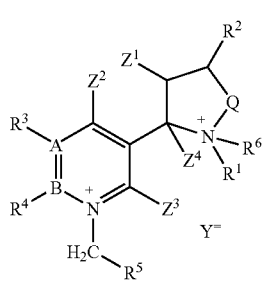

(VI)

wherein

Q is methylene;

$R^1$ is selected from the group consisting of hydrogen, lower straight chain or branched alkyl, cycloalkyl, substituted cycloalkyl, aryl and aralkyl;

$R^2$, $Z^1$ and $Z^4$ are each independently selected from the group consisting of hydrogen, lower alkyl, lower branched alkyl, lower alkenyl, and lower branched alkenyl;

A and B are carbon;

$R^3$, $R^4$, $Z^2$ and $Z^3$ are each independently selected from the group consisting of hydrogen; alkyl; substituted alkyl; cycloalkyl; substituted cycloalkyl; substituted alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl;

$R^5$ is selected from the group consisting of alkyl; substituted alkyl; cycloalkyl; substituted cycloalkyl; alkenyl; substituted alkenyl; alkynyl; substituted alkynyl; aryl; substituted aryl; arylalkyl; substituted arylalkyl; arylalkenyl; substituted arylalkenyl; arylalkynyl; substituted arylalkynyl, with the proviso that $R^5$ of R optical isomer of Formula (VI) is not —CH₂OH when A and B are carbon, and $R^5$ of the S optical isomer of Formula (VI) is not hydrogen, —CH₂NH₂ or —CH₂Ph when A and B are carbon;

$R^6$ is hydrogen; and

Y is selected from the group consisting of 2Cl, 2Br, 2I, 2HSO₄, SO₂, 2CH₃SO₃, 2p-TsO and 2CF₃SO₃.

2. The compound according to claim 1, wherein said compound is (S)-trans-3-(1-methyl-pyrrolidin-2-yl)-1-oct-3-enyl-pyridinium bromide hydrobromide salt.

3. The compound according to claim 1, wherein said compound is (S)-trans-1-dec-4-enyl-3-(1-methyl-pyrrolidin-2-yl)-pyridinium bromide.

4. The compound according to claim 1, wherein said compound is (S)-cis-3-(1-methyl-pyrrolidin-2-yl)-1-oct-3-enyl-pyridinium bromide hydrobromide salt.

5. The compound according to claim 1, wherein said compound is (S)-cis-1-dec-4-enyl-3-(1-methyl-pyrrolidin-2-yl)-pyridinium bromide hydrobromide salt.

6. The compound according to claim 1, wherein said compound is (S)-1-dec-9-enyl-3-(1-methyl-pyrrolidin-2-yl)-pyridinium bromide.

7. The compound according to claim 1, wherein said compound is (S)-1-(6-cyclobutyl-hexyl)-3-(1-methyl-pyrrolidin-2-yl)-pyridinium bromide hydrobromide salt.

8. The compound according to claim 1, wherein said compound is (S)-1-(6-cyclopentyl-hexyl)-3-(1-methyl-pyrrolidin-2-yl)-pyridinium bromide hydrobromide salt.

9. The compound according to claim 1, wherein said compound is (S)-1-(6-cyclohexyl-hexyl)-3-(1-methyl-pyrrolidin-2-yl)-pyridinium bromide hydrobromide salt.

10. The compound according to claim 1, wherein said compound is (S)-1-(7-methyl-oct-6-enyl)-3-(1-methyl-pyrrolidin-2-yl)-pyridinium bromide hydrobromide.

11. The compound according to claim 1, wherein said compound is (S)-1-(7-methyl-octyl)-3-(1-methyl-pyrrolidin-2-yl)-pyridinium bromide hydrobromide salt.

12. The compound according to claim 1, wherein $R^1$ is hydrogen or straight chain or branched alkyl having 1–10 carbons, $R^5$ is a branched or non-branched $C_4$–$C_{19}$ alkyl having 4–19 carbons, cycloalkyl, alkenyl, alkynyl, aryl, arylalkyl, arylalkenyl or arylalkynyl; and Y is 2Br or 2I.

13. The compound according to claim 1, wherein $R^1$ is methyl, ethyl, isopropyl or isobutyl; $R^2$ is hydrogen; and $R^3$ and $R^4$ are individually hydrogen, halogen, alkyl or alkyol, $R^5$ is a branched or non-branched $C^4$–$C^{19}$ alkyl having 4–19 carbons, cycloalkyl, alkenyl, alkynyl, aryl, arylalkyl, arylalkenyl or arylalkynyl; $Z^1$, $Z^2$, $Z^3$ and $Z^4$ hydrogen; Y is 2Br or 2I.

14. The compound according to claim 1, wherein $R^1$ is methyl; $R^2$ is hydrogen; and $R^3$ and $R^4$ are individually hydrogen, halogen, alkyl or alkyol, $R^5$ is a branched or non-branched $C_4$–$C_{19}$ alkyl having 4–19 carbons, cycloalkyl, alkenyl, alkynyl, aryl, arylalkyl, arylalkenyl or arylalkynyl; $Z^1$, $Z^2$, $Z^3$ and $Z^4$ are hydrogen; and Y is 2Br or 2I.

15. The compound according to claim 1, wherein said compound is substantially optically pure.

* * * * *